United States Patent
Manoharan et al.

(10) Patent No.: US 10,119,136 B2
(45) Date of Patent: Nov. 6, 2018

(54) RNAI AGENTS MODIFIED AT THE 4'-C POSITION

(71) Applicant: ALNYLAM PHARMACEUTICALS, INC., Cambridge, MA (US)

(72) Inventors: Muthiah Manoharan, Cambridge, MA (US); Shigeo Matsuda, Cambridge, MA (US); Kallanthottathil G. Rajeev, Cambridge, MA (US); Ivan Zlatev, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/110,658

(22) PCT Filed: Jan. 9, 2015

(86) PCT No.: PCT/US2015/010858
§ 371 (c)(1),
(2) Date: Jul. 8, 2016

(87) PCT Pub. No.: WO2015/106128
PCT Pub. Date: Jul. 16, 2015

(65) Prior Publication Data
US 2017/0029815 A1 Feb. 2, 2017

Related U.S. Application Data

(60) Provisional application No. 61/925,369, filed on Jan. 9, 2014.

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/14* (2013.01); *C12N 2310/315* (2013.01); *C12N 2310/3125* (2013.01); *C12N 2310/32* (2013.01); *C12N 2310/321* (2013.01); *C12N 2310/33* (2013.01); *C12N 2310/335* (2013.01); *C12N 2310/341* (2013.01); *C12N 2310/343* (2013.01); *C12N 2310/344* (2013.01); *C12N 2310/346* (2013.01); *C12N 2310/351* (2013.01); *C12N 2320/51* (2013.01); *C12N 2320/53* (2013.01)

(58) Field of Classification Search
None
See application file for complete search history.

(56) References Cited

U.S. PATENT DOCUMENTS

| | | | |
|---|---|---|---|
| 2009/0182136 A1* | 7/2009 | Wengel | C12N 15/111 536/24.5 |
| 2010/0047909 A1* | 2/2010 | Quay | C12N 15/1131 435/375 |
| 2011/0152353 A1* | 6/2011 | Koizumi | A61K 31/713 514/44 A |
| 2016/0272972 A1* | 9/2016 | Smith | C12N 15/111 |

FOREIGN PATENT DOCUMENTS

| | | |
|---|---|---|
| WO | 96/14329 | 5/1996 |
| WO | 2005/121368 A1 | 12/2005 |
| WO | 2009/073809 A2 | 6/2009 |
| WO | 2010/065756 A2 | 6/2010 |
| WO | 2013/074974 A2 | 5/2013 |

OTHER PUBLICATIONS

Hamada et al. (Antisense & Nucleic Acid Drug Development (2002), 12(5), 301-309).*
Gore et al., "Synthesis, Gene Silencing, and Molecular Modeling Studies of 4'-C-Aminomethyl-2'-O-methyl Modified Small Interfering RNAs", J. Org. Chem. 77:3233-3245 (2012).
Nawale et al., "Incorporation of 4'-C-aminomethyl-2'-O-methylthymidine into DNA by thermophilic DNA polymerases", Chem. Commun. 48:9619-9621 (2012).

\* cited by examiner

*Primary Examiner* — Kimberly Chong
(74) *Attorney, Agent, or Firm* — Jeffrey N. Townes; Cozen O'Connor

(57) ABSTRACT

One aspect of the present invention relates to double-stranded RNAi (dsRNA) duplex agent capable of inhibiting the expression of a target gene in vivo. The dsRNA duplex comprises one or more 4'-modifications in one or both strand. Other aspects of the invention relates to pharmaceutical compositions comprising these dsRNA agents suitable for in vivo therapeutic use, and methods of inhibiting the expression of a target gene by administering these dsRNA agents, e.g., for the treatment of various disease conditions.

18 Claims, 2 Drawing Sheets
Specification includes a Sequence Listing.

RNAI AGENTS MODIFIED AT THE 4'-C POSITION

CROSS-REFERENCE TO RELATED APPLICATIONS

This application is a national-stage application under 35 U.S.C. § 371 of PCT Application No. PCT/US2015/010858, filed Jan. 9, 2015, which claims priority to U.S. Provisional Application No. 61/925,369, filed Jan. 9, 2014, which are hereby incorporated by reference in their entirety.

FIELD OF THE INVENTION

The invention relates RNAi duplex agents having particular motifs that are advantageous for inhibition of target gene expression in vivo, as well as RNAi compositions suitable for in vivo therapeutic use. Additionally, the invention provides methods of inhibiting the expression of a target gene by administering these RNAi duplex agents, e.g., for the treatment of various diseases.

BACKGROUND

RNA interference or "RNAi" is a term initially coined by Fire and co-workers to describe the observation that double-stranded RNAi (dsRNA) can block gene expression (Fire et al. (1998) *Nature* 391, 806-811; Elbashir et al. (2001) *Genes Dev.* 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

Double-stranded RNA (dsRNA) molecules with good gene-silencing properties are needed for drug development based on RNA interference (RNAi). An initial step in RNAi is the activation of the RNA induced silencing complex (RISC), which requires degradation of the sense strand of the dsRNA duplex. Sense strand was known to act as the first RISC substrate that is cleaved by Argonaute 2 in the middle of the duplex region. Immediately after the cleaved 5'-end and 3'-end fragments of the sense strand are removed from the endonuclease Ago2, the RISC becomes activated by the antisense strand (Rand et al. (2005) *Cell* 123, 621).

It was believed that when the cleavage of the sense strand is inhibited, the endonucleolytic cleavage of target mRNA is impaired (Leuschner et al. (2006) *EMBO Rep.*, 7, 314; Rand et al. (2005) *Cell* 123, 621; Schwarz et al. (2004) *Curr. Biol.* 14, 787). Leuschner et al. showed that incorporation of a 2'-O-Me ribose to the Ago2 cleavage site in the sense strand inhibits RNAi in HeLa cells (Leuschner et al. (2006) *EMBO Rep.*, 7, 314). A similar effect was observed with phosphorothioate modifications, showing that cleavage of the sense strand is absolutely required for efficient RNAi also in mammals.

Chemical modifications offer "drug-like" properties and modulate therapeutic characteristics such as biostability, immune stimulation and pharmacology of short interfering RNAs (siRNA). The acceptance of extent of chemical modification on sense (or passenger) and antisense (or guide) strands are determined by the nature of the modification and positional placement of the chemical modification in the oligonucleotide sequence in each strand. There is thus an ongoing need for iRNA duplex agents to improve the gene silencing efficacy of siRNA gene therapeutics. This invention is directed to that need.

SUMMARY

Disclosed herein are oligonucleotides comprising 4'-modified moieties for RNA interference. The modifications are present on the sense strand on the antisense strand or on both the sense strand and the antisense strand thereby imparting on the molecules beneficial properties including one or more of increased knock down activity of target gene expression, increased stability to endo- and or exonucleases (i.e. act as a capping moiety), reduced off-target effects and/or lack of immunomodulating effects and are useful in the treatment of subjects suffering from diseases or conditions and or symptoms associated with such diseases or conditions or at risk of contracting diseases or conditions in which target gene expression has adverse consequences.

DETAILED DESCRIPTION

Figure 1:
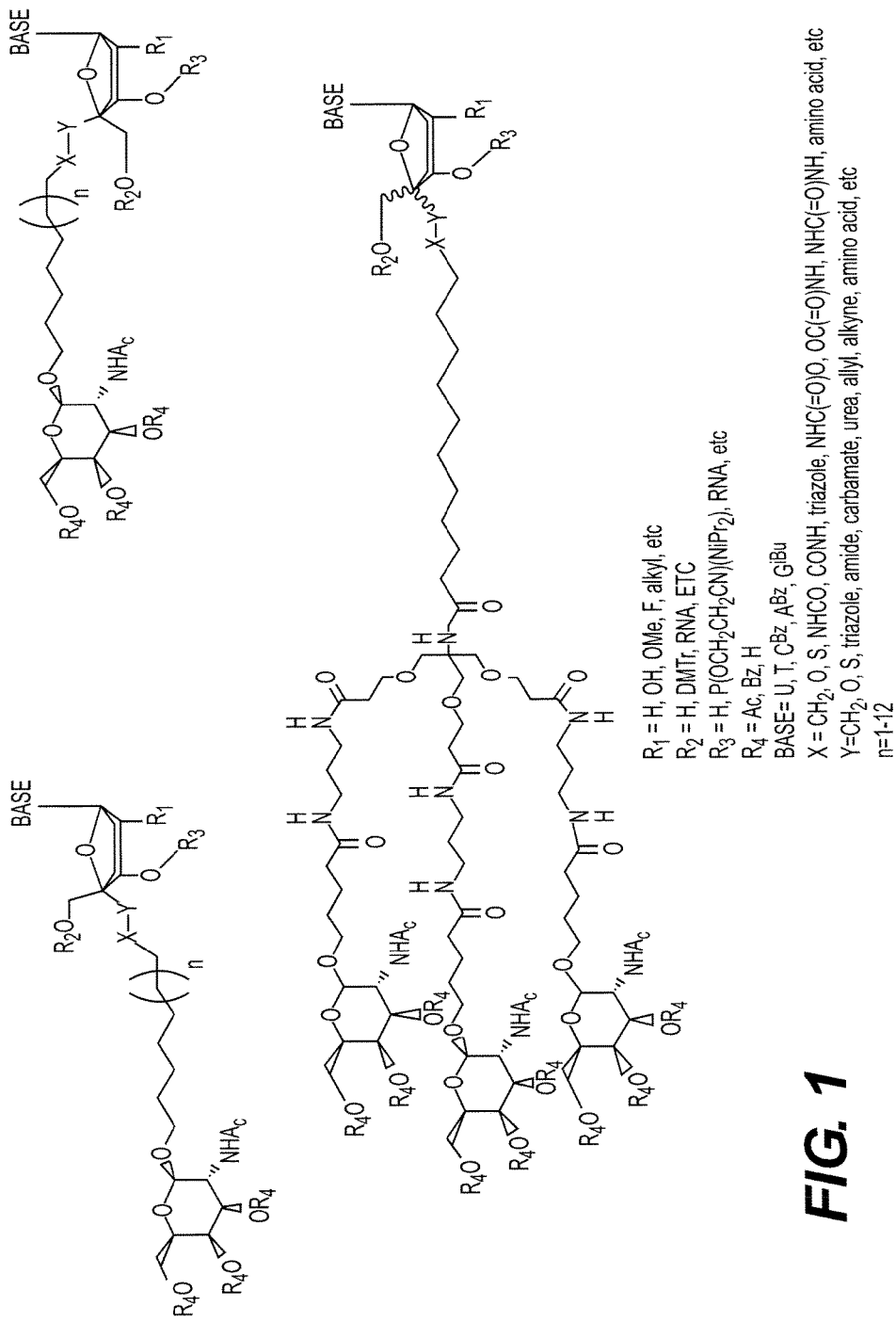
FIG. 1 shows possible 4'- and 5'-conjugates from 4'-modified nucleotide building blocks.

In one embodiment, one or more of 4'-modifications is incorporated into a sense strand and/or antisense strand of a dsRNA agent. The dsRNA agent optionally conjugates with a GalNAc derivative ligand, for instance on the sense strand. The resulting dsRNA agents present superior gene silencing activity, or maintain the silencing activity but provide stability to endo- and or exonucleases, reduced off-target effects and/or lack of immunomodulating effects.

In one embodiment, the invention provides a double-stranded RNAi (dsRNA) agent comprising one or more 4'-modified nucleoside capable of inhibiting the expression of a target gene in vivo. The dsRNA agent comprises a sense strand and an antisense strand. Each strand of the dsRNA agent can range from 12-30 nucleotides in length. For example, each strand can be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. The sense strand and antisense strand typically form a duplex dsRNA. The duplex region of a dsRNA agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27. The dsRNA agent may contain one or more overhang regions and/or capping groups of dsRNA agent at 3'-end, or 5'-end or both ends of a strand. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In one embodiment, the 4'-modified nucleoside is represented by one the following formulas in group i) or group ii):

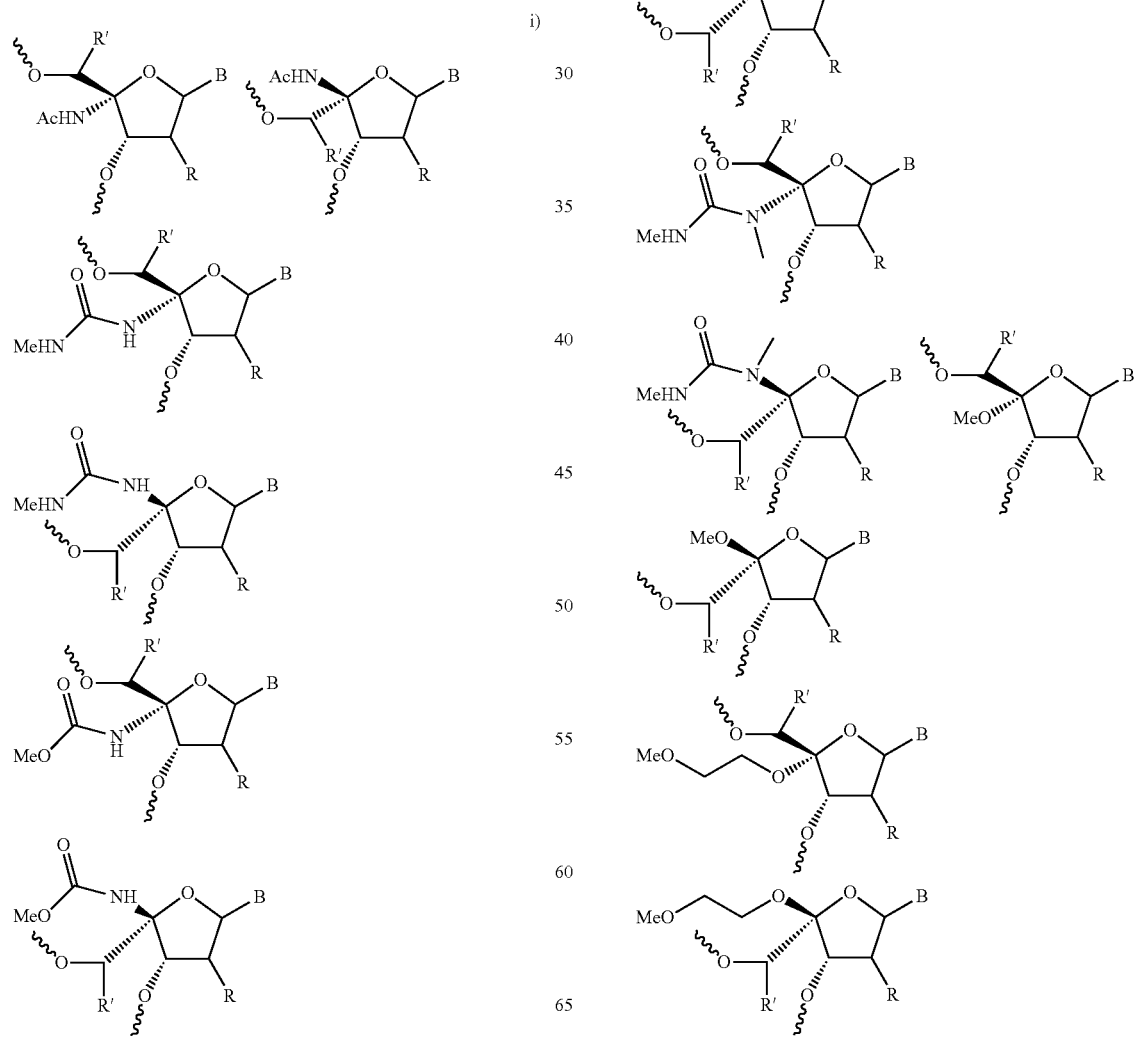

-continued
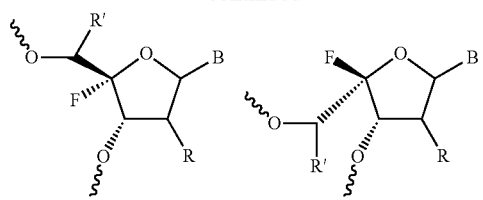
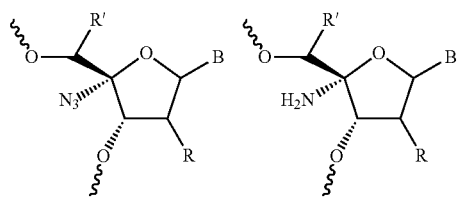
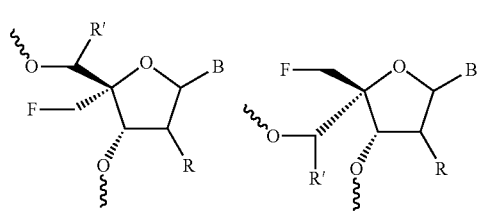
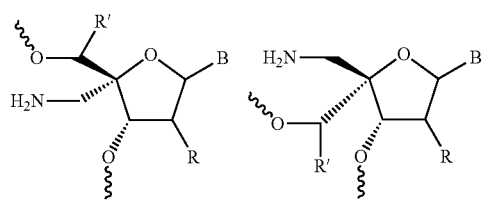
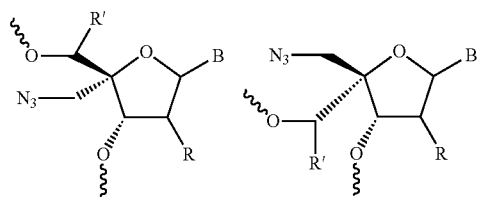
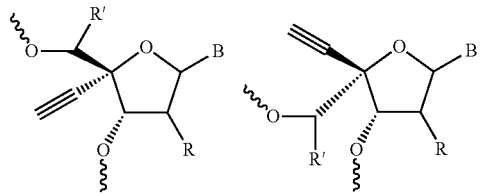
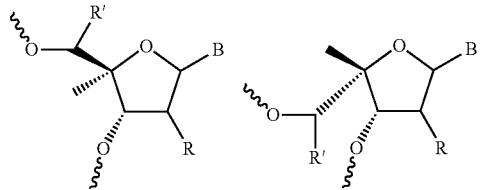
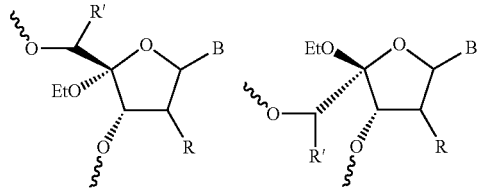
-continued
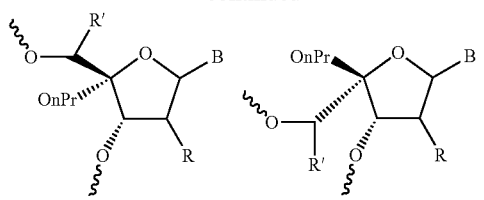
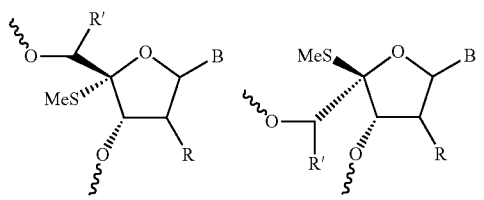
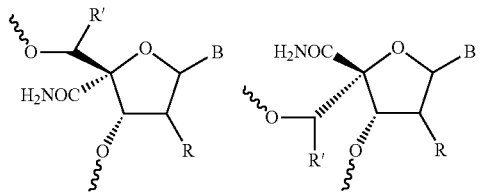
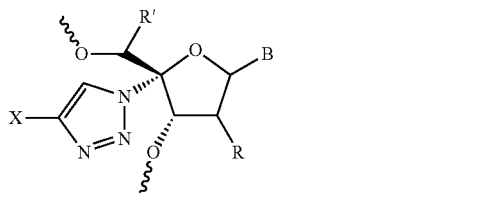
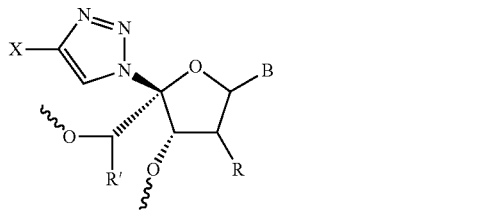
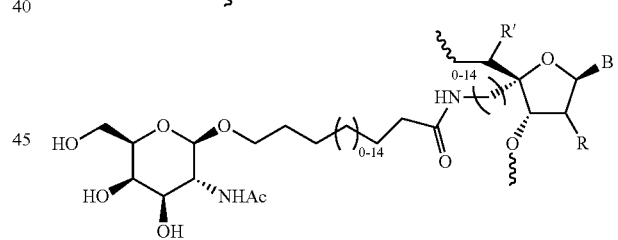
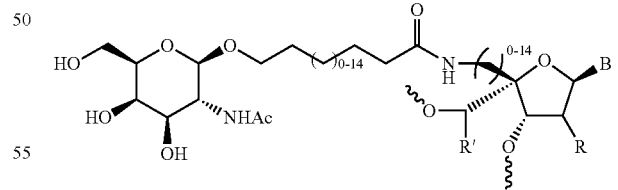
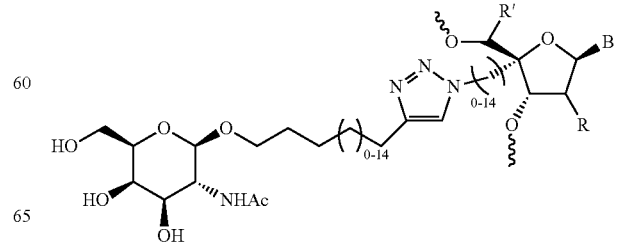

-continued

[Chemical structure diagrams]

wherein:

R=H; OMe; F; OH; O—(CH$_2$)$_2$OMe; SMe, NMe$_2$; NH$_2$; Me; O-nPr; O-alkyl; O-alkylamino;

alternatively R is O—CH$_2$C(O)NH-Me; O—(CH$_2$)$_2$NMe$_2$; or O—(CH$_2$)$_2$O—(CH$_2$)$_2$NMe$_2$;

R'=H, Me; and

B=A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles, Y and Y'=each independently for each occurrence absent, CO, NH, O, S, OC(O), NHC(O), CH$_2$, CH$_2$NH or CH$_2$O, O, S, S(O), SO$_2$, N(R$^N$), C(R')=C(R"), C≡C or C(O), NHCH(R)C(O), —C(O)—CH(R)—NH—, CO, CH=N—O,

[Chemical structures]

or heterocyclyl;

n=entire number from 0 to 14;

L=represent the ligand; i.e. each independently for each occurrence a monosaccharide (such as GalNAc), disaccharide, trisaccharide, tetrasaccharide, oligosaccharide, or polysaccharide; peptide, oligopeptide, RGD peptide, peptidoid; folate; cholesterol, lipid or heterocycle.

wherein the stereochemistry is R or S and combinations of R and S for the unspecified chiral centers;

or ii)

[Chemical structure diagrams]

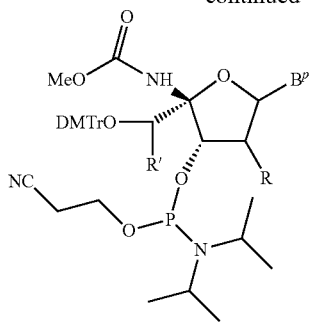
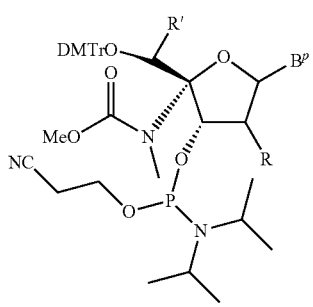
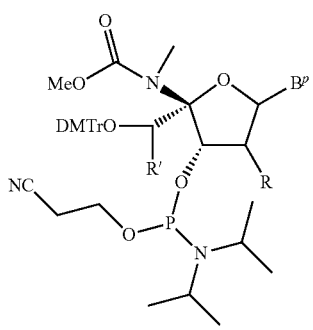
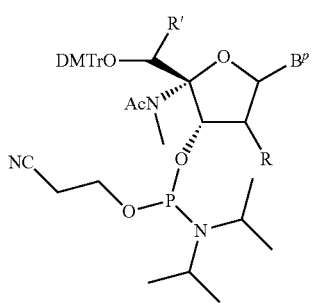
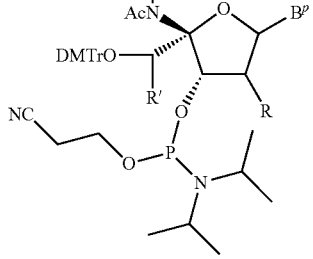
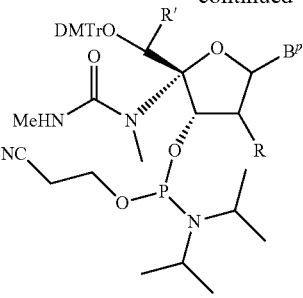
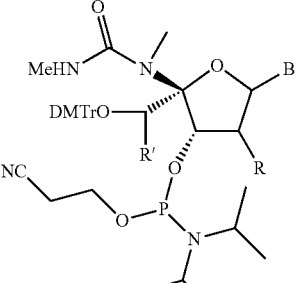
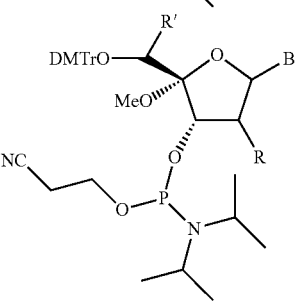
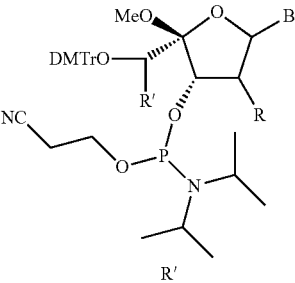
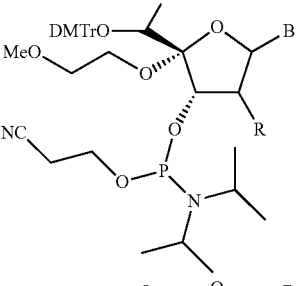
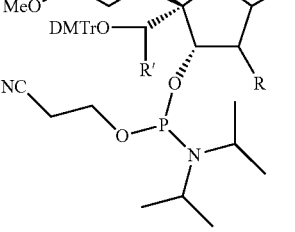

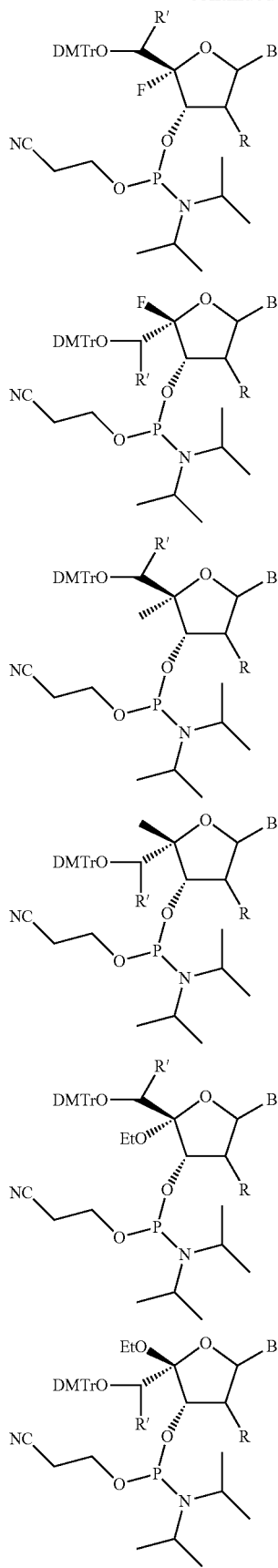
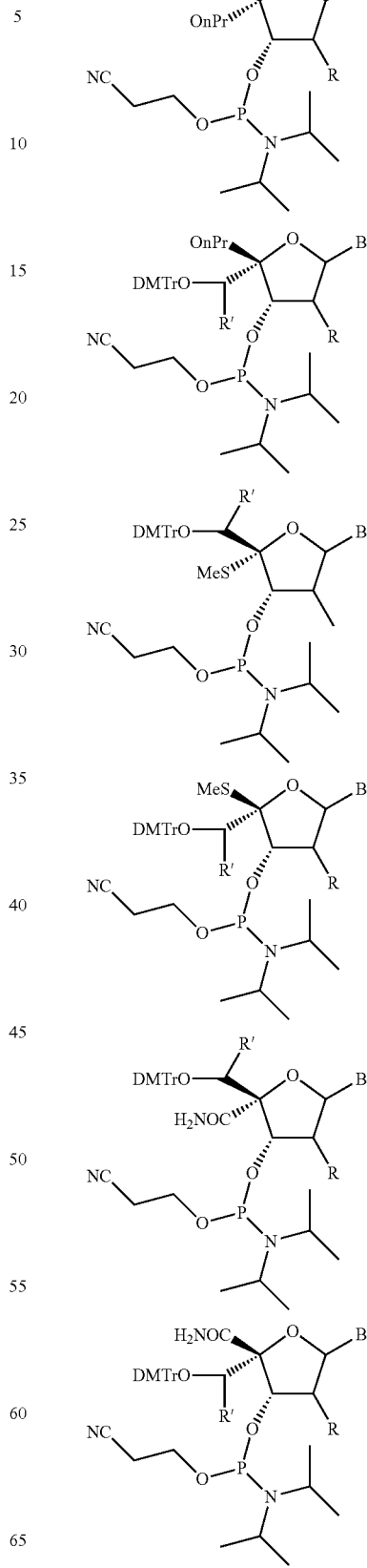

-continued

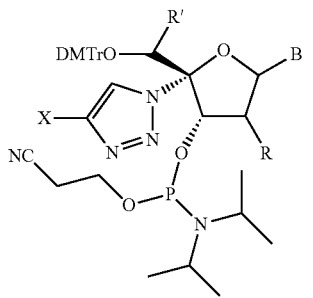

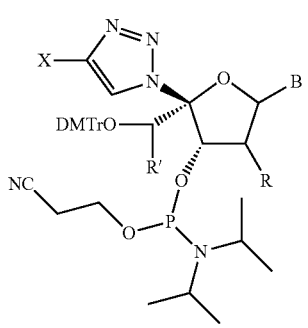

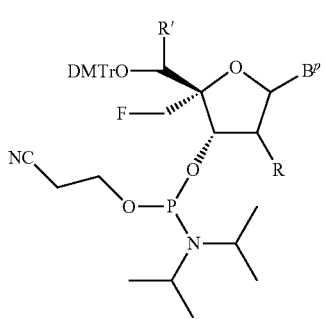

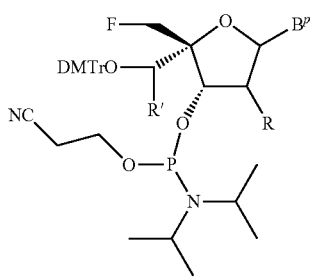

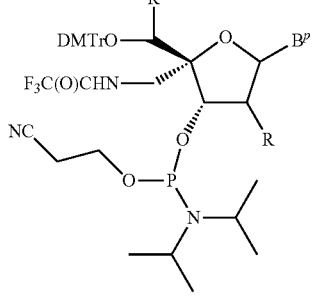

-continued

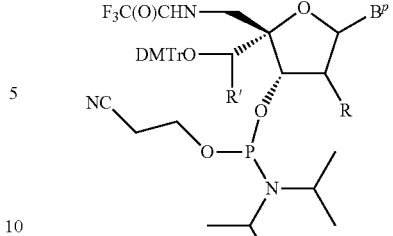

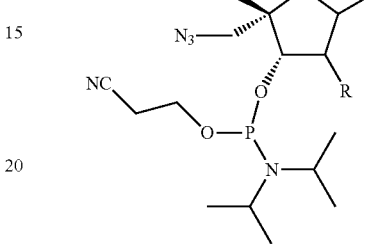

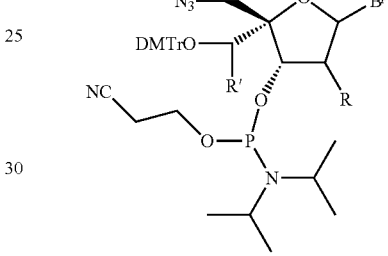

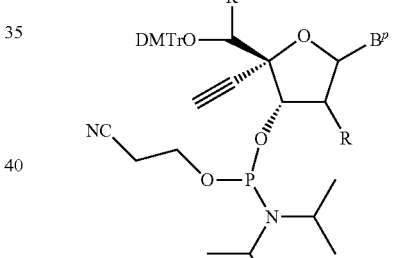

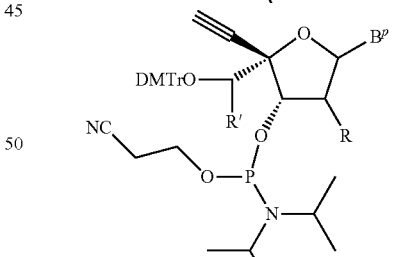

wherein:
R=H; OMe; OEt, F; OTBDMS; O—(CH$_2$)$_2$OMe; SMe, NMe$_2$; NPhth; Me; O-nPr; O-alkyl; O-alkylamino;
alternatively, R is O—CH2C(O)NHMe; O—(CH2)2NMe2; or O—(CH2)2O—(CH2)2 NMe2;
R'=H, Me; and
B$^p$ or B=A$^{Bz}$; C$^{Ac}$; 5-Me-C$^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles, wherein the stereochemistry is R or S and combinations of R and S for the unspecified chiral centers.

In one embodiment, the 4'-modified nucleoside is within the 2, 3, 4, 5 or 6 of termini nucleotides at the 3' and/or 5' of the sense and/or antisense.

In one embodiment, the 4'-modified nucleoside is within the 2, 3, 4, 5 or 6 of termini of the duplex region of the dsRNA agent at the 3' and/or 5' of the sense and/or antisense.

In one embodiment, the sense strand comprises 1, 2, 3, 4, 5, 6, 7, 8, 9 or 10 4'-modified nucleic acid moieties at the 3' terminal or penultimate positions of the sense strand. In one embodiment the sense strand comprises threose nucleic acid moieties in positions 18-19, 17-18, 16-17, or 15-16 from the 5' terminus. In one embodiment the sense strand comprises 4'-modified nucleic acid moieties in positions 15-17, 15-18 or 15-19 from the 5' terminus. In one embodiment the sense strand comprises 4'-modified nucleic acid moieties in positions 11-19, 12-19, 13-19, 14-19, 15-19, 16-19, 17-19, from the 5' terminus. In one embodiment the sense strand comprises 4'-modified nucleic acid moieties in positions 11-18, 12-18, 13-18, 14-18, 15-18, 16-18 from the 5' terminus.

In one embodiment, the sense strand comprises at least one 4'-modified nucleic acid moieties within 1, 2, 3 or 4 position at the 3' terminal or penultimate positions of the sense strand, antisense strand, or both strands.

In one embodiment, the sense strand comprises at least one or two 4'-modified nucleic acid moieties within 2 and/or 3 position at the 3' terminal or penultimate positions of the sense strand, antisense strand, or both strands.

In one embodiment, the sense strand comprises at least one 4'-modified nucleic acid moieties within 1, 2, 3 or 4 position at the 5' terminal or penultimate positions of the sense strand, antisense strand, or both strands.

In one embodiment, the sense strand comprises at least one or two 4'-modified nucleic acid moieties within 2 and/or 3 position at the 5' terminal or penultimate positions of the sense strand, antisense strand, or both strands.

In one embodiment, when the sense strand comprises at least one 4'-modified nucleic acid moieties within the internal position of the duplex, the corresponding antisense strand comprises the corresponding 4'-modified nucleic acid moieties such that the modified nucleosides from the sense strands and the antisense strand are complementary to each other. For example, the 4'-modified nucleoside in the sense strand can be base paired with the 4'-modified nucleoside of the antisense strand.

In one embodiment, when the sense strand comprises at least one 4'-modified nucleic acid moieties within the internal position of the duplex, the corresponding antisense strand comprises the corresponding 4'-modified nucleic acid moieties such that the modified nucleosides from the sense strands and the antisense strand are not base paired to each other.

The above embodiments for 4'-modifications on nucleic acid moieties can be used for either single-stranded or double-stranded iRNA agent.

In one embodiment, the 4'-modified nucleoside can be used in a single-stranded RNAi agent, miRNA, or miRNA mimetic. In one embodiment, the single-stranded RNAi agent, miRNA, or miRNA mimetic agent comprises at least one 4'-modified nucleic acid moieties within 1, 2, 3 or 4 position at the 3' terminal or penultimate positions of the strand. In one embodiment, the single-stranded RNAi agent, miRNA, or miRNA mimetic comprises at least one or two 4'-modified nucleic acid moieties within 2 and/or 3 position at the 3' terminal or penultimate positions of the strand. In one embodiment, the single-stranded RNAi agent, miRNA, or miRNA mimetic comprises at least one 4'-modified nucleic acid moieties within 1, 2, 3 or 4 position at the 5' terminal or penultimate positions of the strand. In one embodiment, the single-stranded RNAi agent, miRNA, or miRNA mimetic agent comprises at least one or two 4'-modified nucleic acid moieties within 2 and/or 3 position at the 5' terminal or penultimate positions of the strand.

In one embodiment, the 4'-modified nucleoside can be used in an antisense oligonucleotide. In one embodiment, the antisense oligonucleotide comprises at least one 4'-modified nucleic acid moieties within 1, 2, 3 or 4 position at the 3' terminal or penultimate positions of the strand. In one embodiment, the antisense oligonucleotide comprises at least one or two 4'-modified nucleic acid moieties within 2 and/or 3 position at the 3' terminal or penultimate positions of the strand. In one embodiment, the antisense oligonucleotide comprises at least one 4'-modified nucleic acid moieties within 1, 2, 3 or 4 position at the 5' terminal or penultimate positions of the strand. In one embodiment, antisense oligonucleotide comprises at least one or two 4'-modified nucleic acid moieties within 2 and/or 3 position at the 5' terminal or penultimate positions of the strand.

In one embodiment, the 4'-modified nucleoside is selected from one of the following:

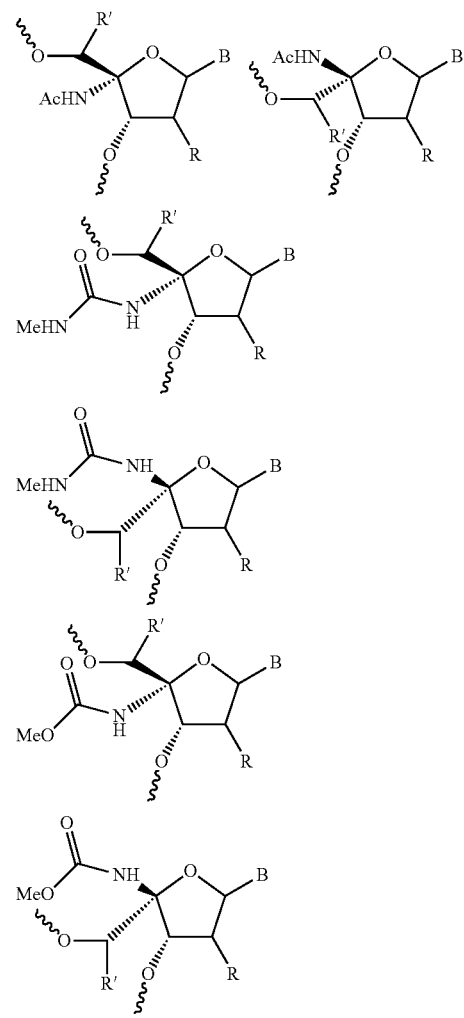

-continued
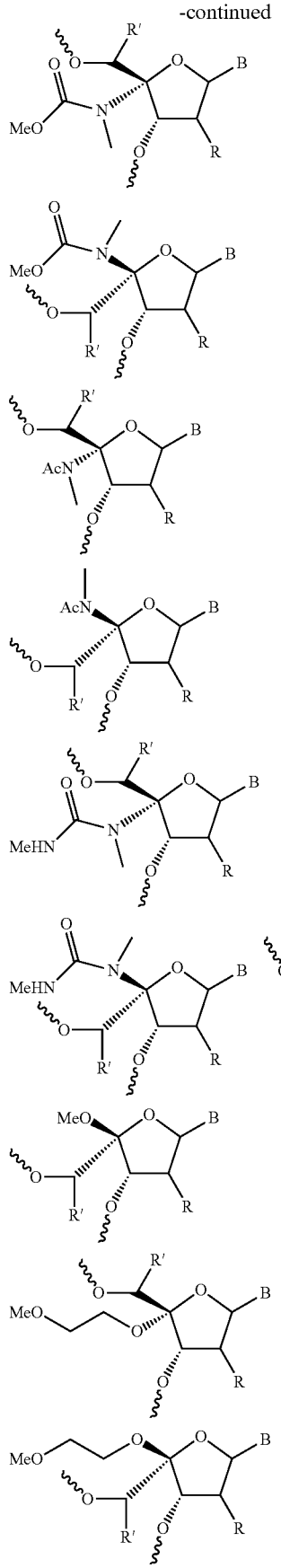
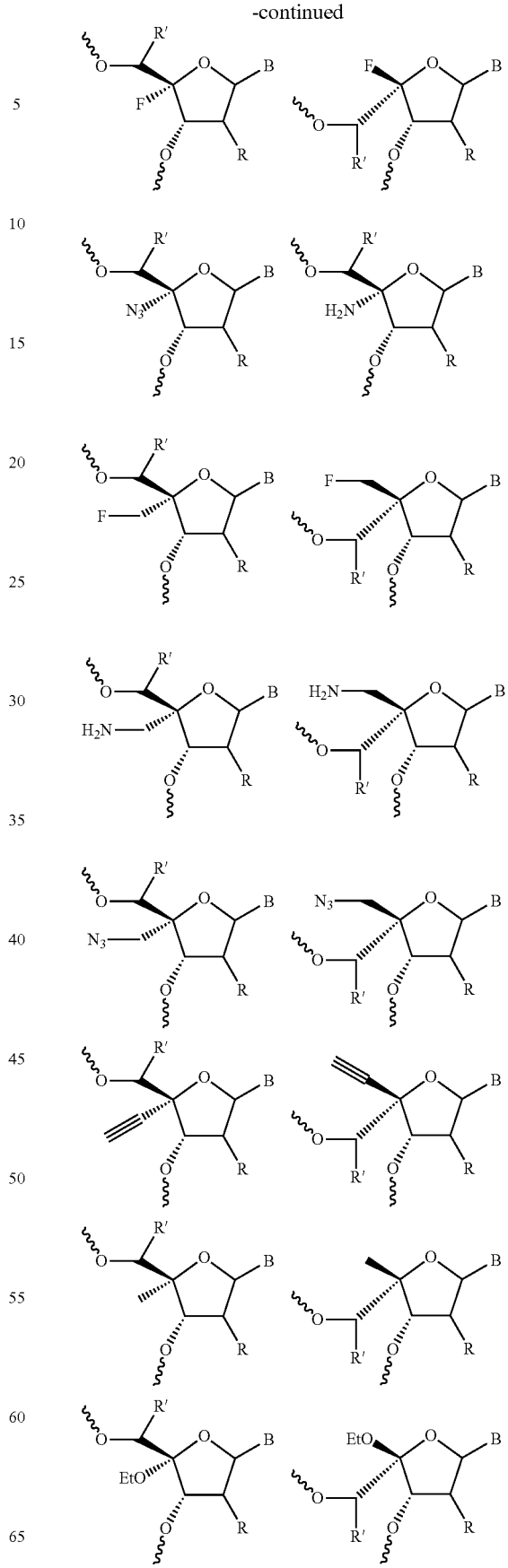

-continued

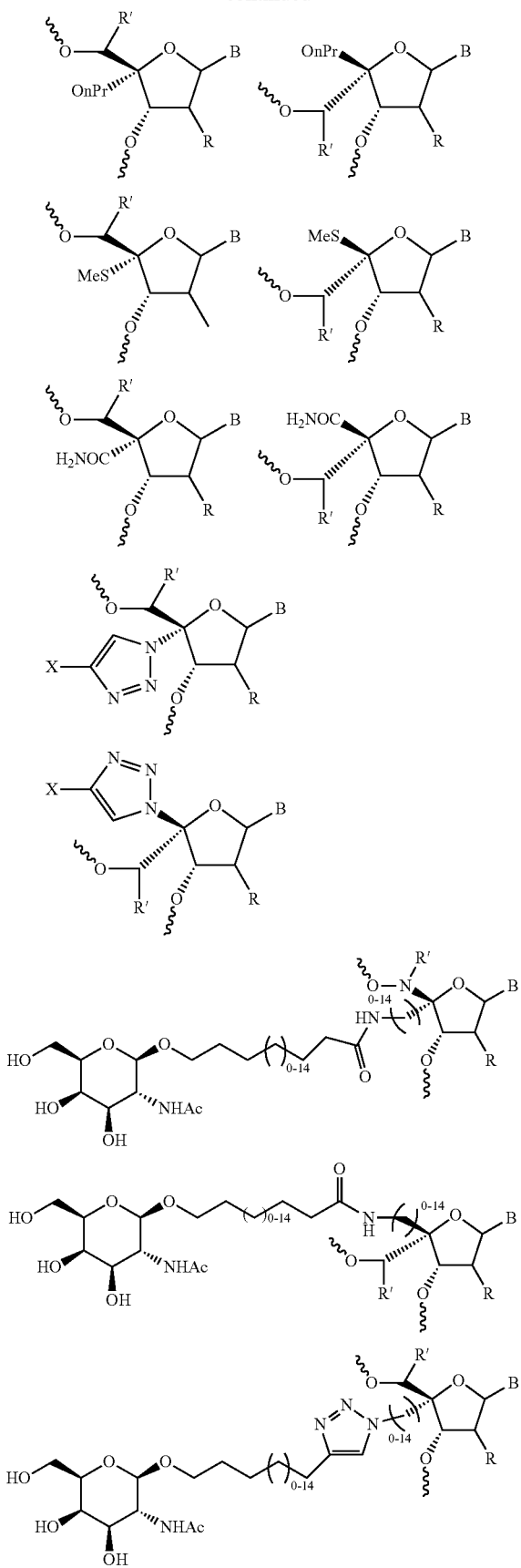

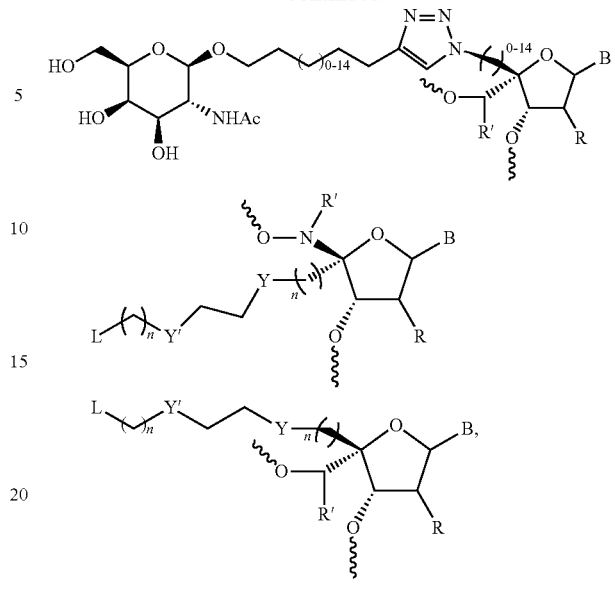

wherein:

R=H; OMe; F; OH; O—(CH$_2$)$_2$OMe; SMe, NMe$_2$; NH$_2$; Me; O-nPr; O-alkyl; O-alkylamino;

alternatively, R is O—CH$_2$C(O)NHMe; O—(CH$_2$)$_2$NMe$_2$; or O—(CH$_2$)$_2$O—(CH$_2$)$_2$NMe$_2$;

R'=H, Me; and

B=A; C; 5-Me-C; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles, Y and Y'=each independently for each occurrence absent, CO, NH, O, S, OC(O), NHC(O), CH$_2$, CH$_2$NH or CH$_2$O, O, S, S(O), SO$_2$, N(R$^N$), C(R')=C(R"), C≡C or C(O), NHCH(R)C(O), —C(O)—CH(R)—NH—, CO, CH=N—O,

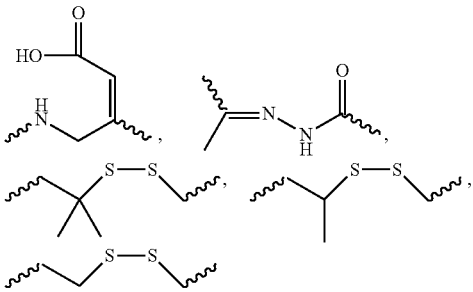

n=entire number from 0 to 14;

L=represent the ligand; i.e. each independently for each occurrence a monosaccharide (such as GalNAc), disaccharide, trisaccharide, tetrasaccharide, oligosaccharide, or polysaccharide; peptide, oligopeptide, RGD peptide, peptidoid, folate, cholesterol, lipid or heterocycle;

wherein the stereochemistry is R or S and combinations of R and S for the unspecified chiral centers.

In one embodiment, the 4'-modified nucleoside is selected from one of the following:

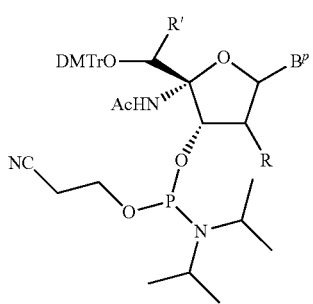
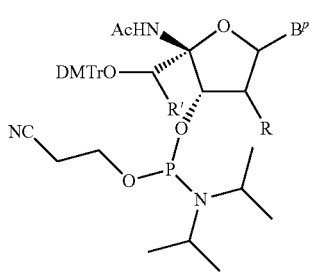
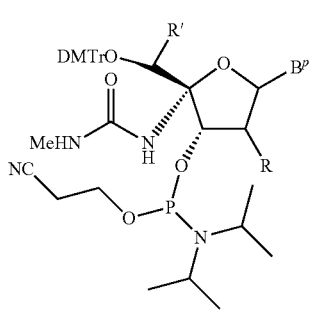
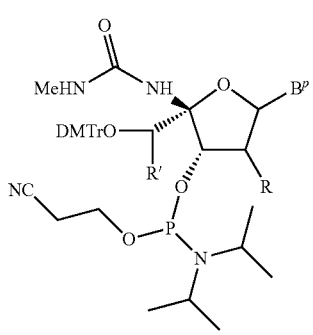
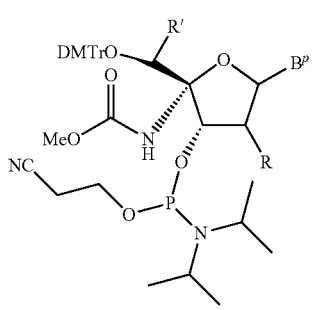
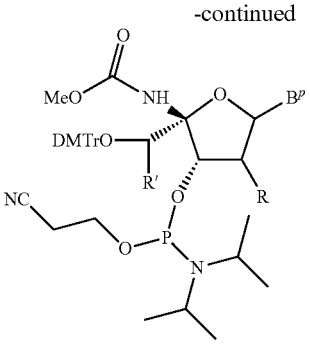
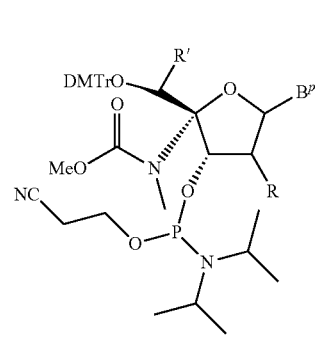
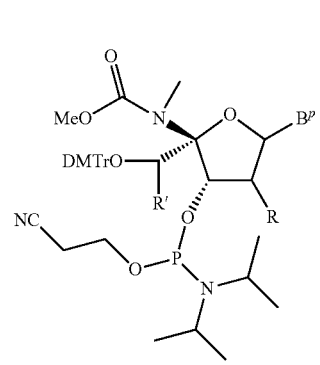
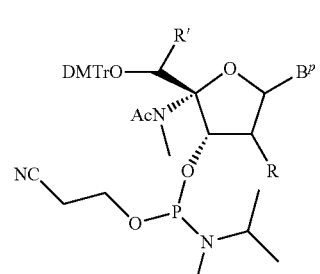
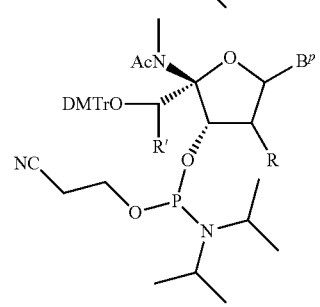

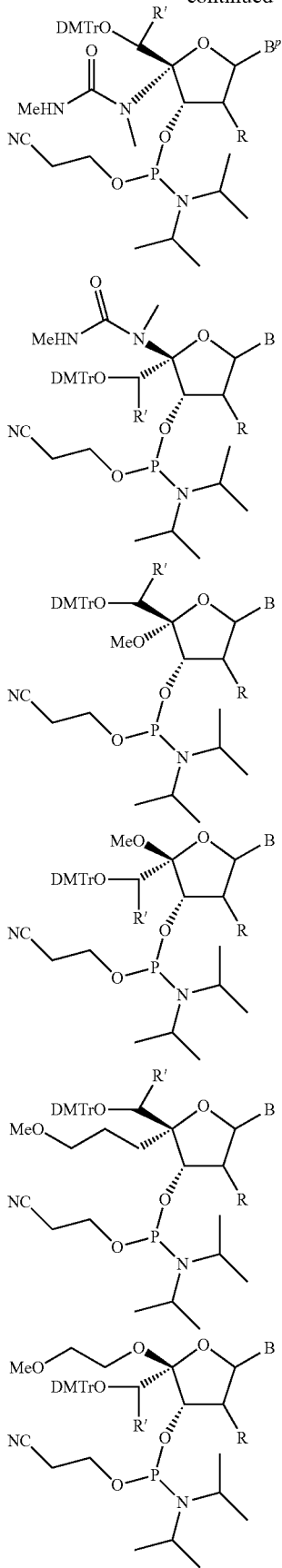
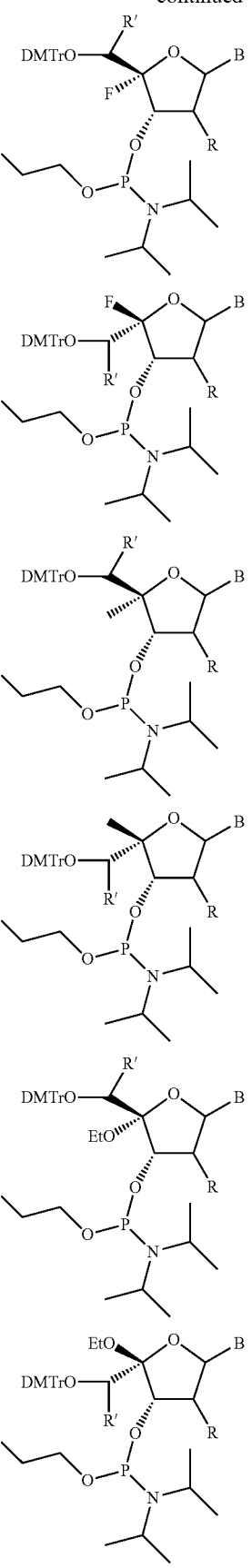

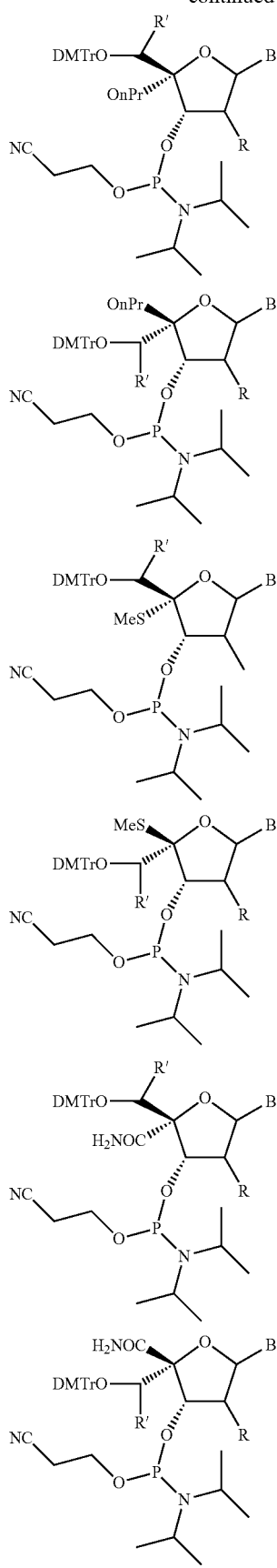
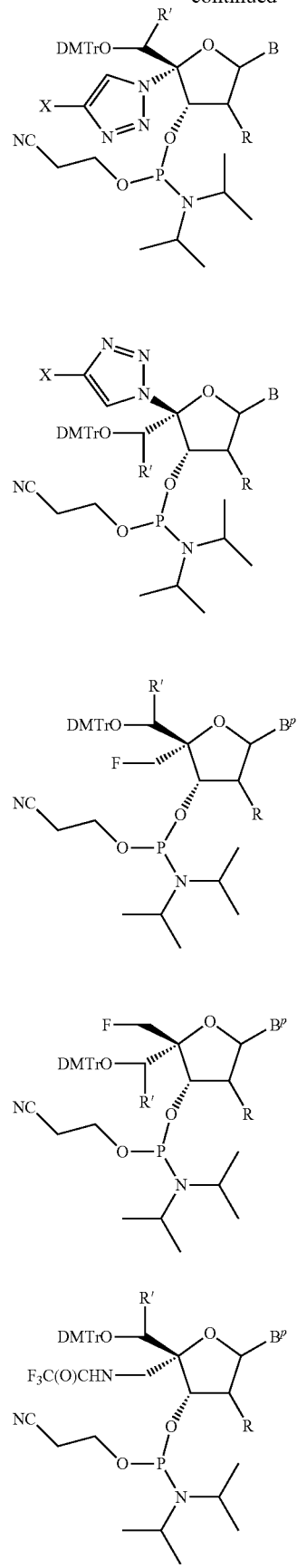

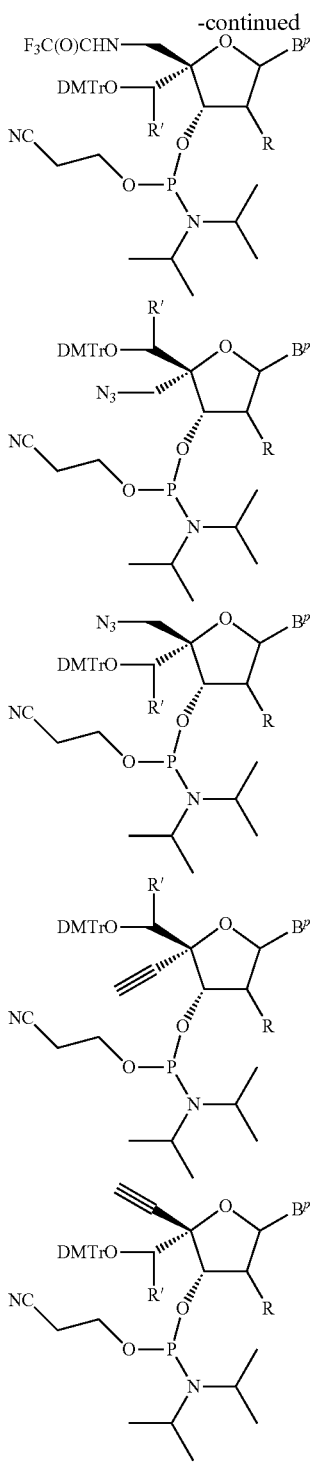

wherein:

R=H; OMe; OEt, F; OTBDMS; O—(CH$_2$)$_2$OMe; SMe, NMe$_2$; NPhth; Me; O-nPr; O-alkyl; O-alkylamino;

alternatively, R is O—CH$_2$C(O)NHMe; O—(CH$_2$)$_2$NMe$_2$; or O—(CH$_2$)$_2$O—(CH$_2$)$_2$NMe$_2$;

R'=H, Me; and

B$^p$ or B=A$^{Bz}$; C$^{Ac}$; 5-Me-C$^{Bz}$; G; I; U; T; Y; 2-thiouridine; 4-thiouridine; C5-modified pyrimidines; C2-modified purines; N8-modified purines; phenoxazine; G-clamp; non-canonical mono, bi and tricyclic heterocycles, wherein the stereochemistry is R or S and combinations of R and S for the unspecified chiral centers.

In one embodiment, the dsRNA agent of the invention is a double ended bluntmer of 19 nt in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In one embodiment, the dsRNA agent of the invention is a double ended bluntmer of 20 nt in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In one embodiment, the dsRNA agent of the invention is a double ended bluntmer of 21 nt in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the dsRNA agent of the invention comprises a 21 nucleotides (nt) sense strand and a 23 nucleotides (nt) antisense, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the dsRNA is blunt, while the other end is comprises a 2 nt overhang. Preferably, the 2 nt overhang is at the 3'-end of the antisense. Optionally, the dsRNA further comprises a ligand (preferably GalNAc$_3$).

In one embodiment, the dsRNA agent of the invention comprises a sense and antisense strands, wherein: the sense strand is 25-30 nucleotide residues in length, wherein starting from the 5' terminal nucleotide (position 1) positions 1 to 23 of said first strand comprise at least 8 ribonucleotides; antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the dsRNA agent of the invention comprises a sense and antisense strands, wherein said dsRNA agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein said 3' end of said first strand and said 5' end of said second strand form a blunt end and said second strand is 1-4 nucleotides longer at its 3' end than the first strand, wherein the duplex region region which is at least 25 nucleotides in length, and said second strand is sufficiently complementary to a target mRNA along at least 19 nt of said second strand length to reduce target gene expression when said dsRNA agent is introduced into a mammalian cell, and wherein dicer cleavage of said dsRNA preferentially results in an siRNA comprising said 3' end of said second strand, thereby reducing expression of the target gene in the mammal. Optionally, the dsRNA agent further comprises a ligand.

In one embodiment, the sense strand of the dsRNA agent contains at least one motif of three identical modifications on three consecutive nucleotides, where one of the motifs occurs at the cleavage site in the sense strand.

In one embodiment, the antisense strand of the dsRNA agent can also contain at least one motif of three identical modifications on three consecutive nucleotides, where one of the motifs occurs at or near the cleavage site in the antisense strand For dsRNA agent having a duplex region of 17-23 nt in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the dsRNA from the 5'-end.

The dsRNA agent of the invention may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internmucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In one embodiment, the dsRNA comprises the phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paried nucleotide next to the overhang nucleotide. Preferably, these terminal three nucleotides may be at the 3'-end of the antisense strand.

In one embodiment, the dsRNA agent of the invention comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the dsRNA agent of the invention comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In one embodiment, the sense strand sequence may be represented by formula (I):

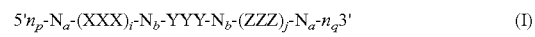  (I)

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification;

wherein at least one of n, N, X, Y, or Z is a 4'-modified nucleoside; and

XXX, YYY and ZZZ each independently represent one motif of three identical modifications on three consecutive nucleotides. Preferably YYY is all 2'-F modified nucleotides.

In one embodiment, the N, and/or $N_b$ comprise modifications of alternating pattern.

In one embodiment, the YYY motif occurs at or near the cleavage site of the sense strand. For example, when the dsRNA agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of the sense strand, the count starting from the 1$^{st}$ nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas, wherein at least one of n, N, X, Y, or Z is a 4'-modified nucleoside:

$$5'n_p\text{-}N_a\text{—}YYY\text{-}N_b\text{-}ZZZ\text{-}N_a\text{-}n_q3' \quad \text{(Ia);}$$

$$5'n_p\text{-}N_a\text{-}XXX\text{-}N_b\text{-}YYY\text{-}N_a\text{-}n_q3' \quad \text{(Ib); or}$$

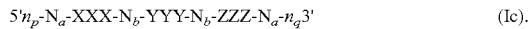

$$5'n_p\text{-}N_a\text{-}XXX\text{-}N_b\text{-}YYY\text{-}N_b\text{-}ZZZ\text{-}N_a\text{-}n_q3' \quad \text{(Ic).}$$

When the sense strand is represented by formula (Ia), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ib), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Ic), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides.

Each of X, Y and Z may be the same or different from each other.

In one embodiment, the antisense strand sequence of the dsRNA may be represented by formula (II):

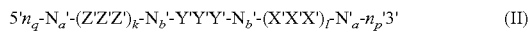

$$5'n_q\text{-}N_a'\text{-}(Z'Z'Z')_k\text{-}N_b'\text{-}Y'Y'Y'\text{-}N_b'\text{-}(X'X'X')_l\text{-}N_a'\text{-}n_p3' \quad \text{(II)}$$

wherein:

k and l are each independently 0 or 1;

p and q are each independently 0-6;

each $N_a'$ independently represents an oligonucleotide sequence comprising 0-25 modified nucleotides, each sequence comprising at least two differently modified nucleotides;

each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification;

wherein at least one of n, N, X, Y, or Z is a 4'-modified nucleoside;

and

X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the dsRNA agent has a duplex region of 17-23 nt in length, the Y'Y'Y' motif can occur at positions 9, 10, 11; 10, 11, 12; 11, 12, 13; 12, 13, 14; or 13, 14, 15 of the antisense strand, with the count starting from the 1$^{st}$ nucleotide, from the 5'-end; or optionally, the count starting at the 1$^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas, wherein at least one of n, N, X, Y, or Z is a 4'-modified nucleoside;

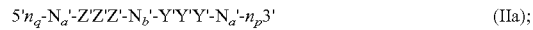

$$5'n_q\text{-}N_a'\text{-}Z'Z'Z'\text{-}N_b'\text{-}Y'Y'Y'\text{-}N_a'\text{-}n_p3' \quad \text{(IIa);}$$

$$5'n_q\text{-}N_b'\text{-}Y'Y'Y'\text{-}N_b'\text{-}X'X'X'\text{-}n_p3' \quad \text{(IIb); or}$$

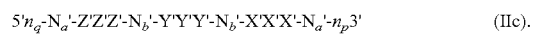

$$5'n_q\text{-}N_a'\text{-}Z'Z'Z'\text{-}N_b'\text{-}Y'Y'Y'\text{-}N_b'\text{-}X'X'X'\text{-}N_a'\text{-}n_p3' \quad \text{(IIc).}$$

When the antisense strand is represented by formula (IIa), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

Each of X', Y' and Z' may be the same or different from each other.

Each nucleotide of the sense strand and antisense strand further comprise LNA, HNA, CeNA, 2'-methoxyethyl, 2'-O-methyl, 2'-O-allyl, 2'-C— allyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification, and at least one of n, N, X, Y, or Z is a 4'-modified nucleoside.

In one embodiment, the sense strand of the dsRNA agent may contain YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification, and at least one of n, N, X, Y, or Z is a 4'-modified nucleoside.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification, and at least one of n, N, X, Y, or Z is a 4'-modified nucleoside.

The sense strand represented by any one of the above formulas (Ia), (Ib) and (Ic) forms a duplex with a antisense strand being represented by any one of formulas (IIa), (IIb) and (IIc), respectively.

Accordingly, the dsRNA agent may comprise a sense strand and an antisense strand, each strand having 14 to 30 nucleotides, the dsRNA duplex represented by formula (III):

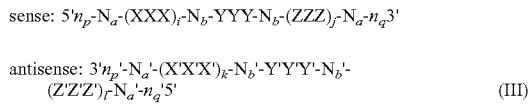

wherein:

i, j, k, and l are each independently 0 or 1;

p and q are each independently 0-6;

each $N_a$ and $N_a'$ independently represents an oligonucleotide sequence comprising 0-25 modified nucleotides, each sequence comprising at least two differently modified nucleotides;

each $N_b$ and $N_b'$ independently represents an oligonucleotide sequence comprising 0-10 modified nucleotides;

wherein at least one of n, N, X, Y, or Z is a 4'-modified nucleoside;

wherein each $n_p'$, $n_p$, $n_q'$, and $n_q$ independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 1 and j is 0; or i is 0 and j is 1; or both i and j are 1. In another embodiment, k is 1 and l is 0; k is 0 and l is 1; or both k and l are 1.

Exemplary combinations of the sense strand and antisense strand forming a dsRNA duplex include the formulas below, wherein at least one of n, N, X, Y, or Z is a 4'-modified nucleoside:

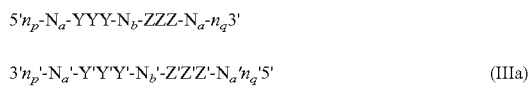

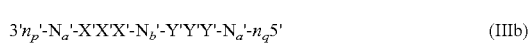

When the dsRNA agent is represented by formula (IIIa), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the dsRNA agent is represented as formula (IIIb), each $N_b$, $N_b'$ independently represents an oligonucleotide sequence comprising 0-10, 0-7, 0-10, 0-7, 0-5, 0-4, 0-2 or 0 modified nucleotides. Each N, independently represents an oligonucleotide sequence comprising 2-20, 2-15, or 2-10 modified nucleotides.

When the dsRNA agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

Each of X, Y and Z in formulas (III), (IIIa), (IIIb) and (IIIc) may be the same or different from each other.

When the dsRNA agent is represented by formula (III), (IIIa), (IIIb) or (IIIc), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the dsRNA agent is represented by formula (IIIa) or (IIIc), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the dsRNA agent is represented as formula (IIIb) or (IIIc), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, the dsRNA agent of the invention is a multimer containing at least two duplexes represented by formula (III), (IIIa), (IIIb) or (IIIc), wherein said duplexes are connected by a linker. The linker can be cleavable or non-cleavable. Optionally, said multimer further comprise a ligand. Each of the dsRNA can target the same gene or two different genes; or each of the dsRNA can target same gene at two different target sites.

In one embodiment, the dsRNA agent of the invention is a multimer containing three, four, five, six or more duplexes represented by formula (III), (IIIa), (IIIb) or (IIIc), wherein said duplexes are connected by a linker. The linker can be cleavable or non-cleavable. Optionally, said multimer further comprises a ligand. Each of the dsRNA can target the same gene or two different genes; or each of the dsRNA can target same gene at two different target sites.

In one embodiment, two dsRNA agent represented by formula (III), (IIIa), (IIIb) or (IIIc) are linked to each other at the 5' end, and one or both of the 3' ends of the are optionally conjugated to a ligand. Each of the dsRNA can target the same gene or two different genes; or each of the dsRNA can target same gene at two different target sites.

Various publications described multimeric siRNA and can all be used with the dsRNA of the invention. Such publications include WO2007/091269, U.S. Pat. No. 7,858,769, WO2010/141511, WO2007/117686, WO2009/014887 and WO2011/031520 which are hereby incorporated by their entirely.

The dsRNA agent that contains conjugations of one or more carbohydrate moieties to a dsRNA agent can optimize one or more properties of the dsRNA agent. In many cases, the carbohydrate moiety will be attached to a modified subunit of the dsRNA agent. E.g., the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In embodiment the dsRNA of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone. The double-stranded RNA (dsRNA) agent of the invention may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

Ligands

A wide variety of entities can be coupled to the oligonucleotides of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g. EDTA), lipophilic molecules, e.g, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP (SEQ ID NO: 1). An RFGF analogue (e.g., amino acid sequence AALLPVLLAAP (SEQ ID NO: 2)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 3)) and the *Drosophila* Antennapedia protein (RQIKI-WFQNRRMKWKK (SEQ ID NO: 4)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues.

For example, a glycosylated RGD peptide can deliver an iRNA agent to a tumor cell expressing $\alpha_v\beta_3$ (Haubner et al., Jour. Nucl. Med., 42:326-336, 2001). Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogeneis. Preferred conjugates of this type lignads that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin Pi), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Examplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbaone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in U.S. patent application Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP—$(CH_2)_n NH_2$ may be incorporated into a growing oligonucelotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylglucosamine) derivatives attached through a bivalent or trivalent branched linker.

In one embodiment, the dsRNA of the invention is conjugated to a bivalent and trivalent branched linkers include the structures shown in any of formula (IV)-(VII):

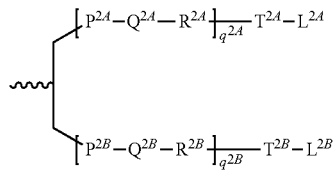

Formula (IV)

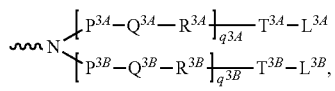

Formula (V)

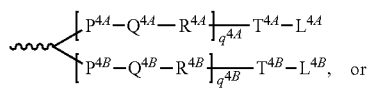

Formula (VI)

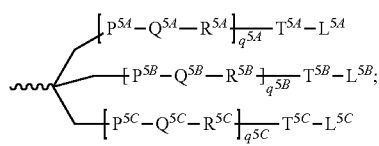

Formula (VII)

wherein:

$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherin one or more methylenes can be interrupted or terminated by one or more of O, S, S(O), $SO_2$, $N(R^N)$, C(R')=C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, NHCH($R^a$)C(O), —C(O)—CH($R^a$)—NH—, CO, CH=N—O,

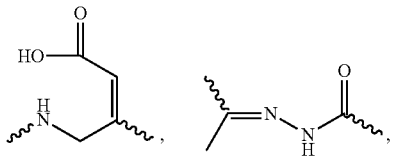

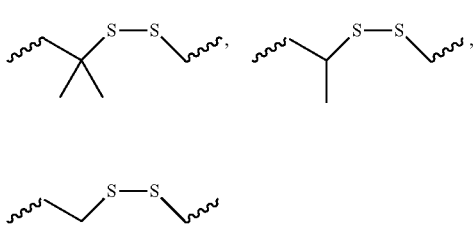

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

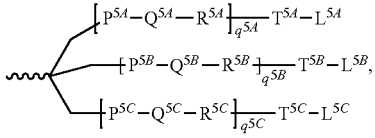

Formula (VII)

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the following compounds:

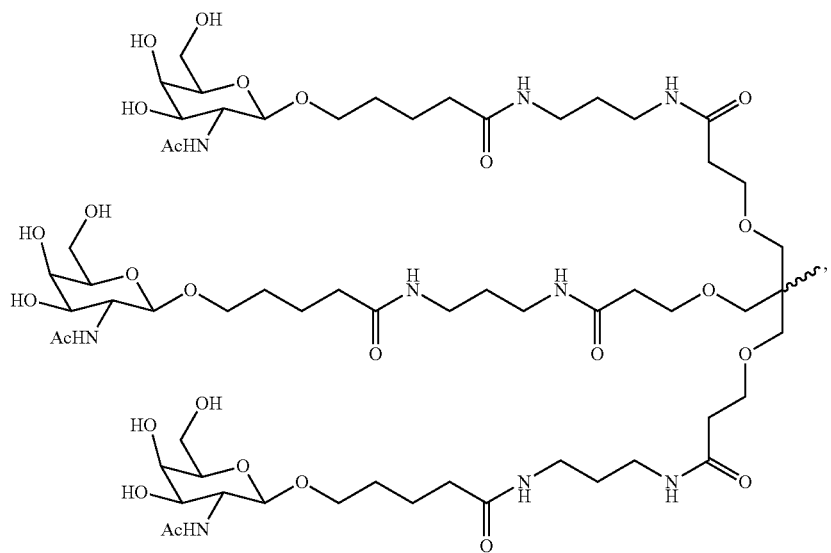
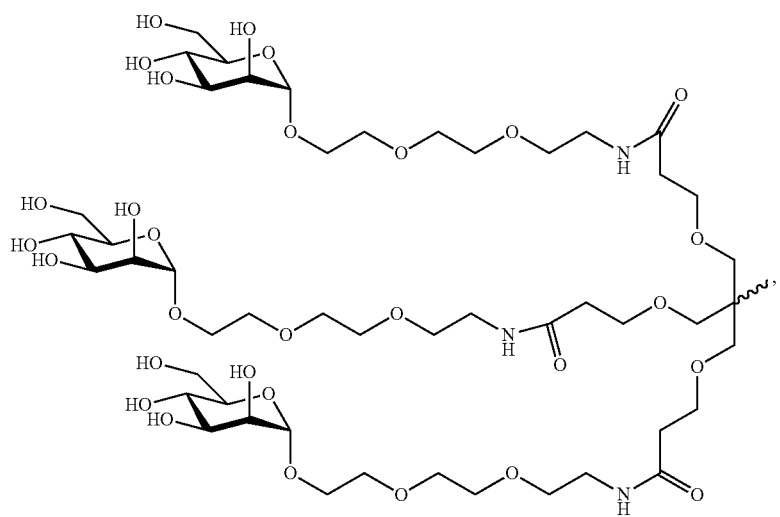
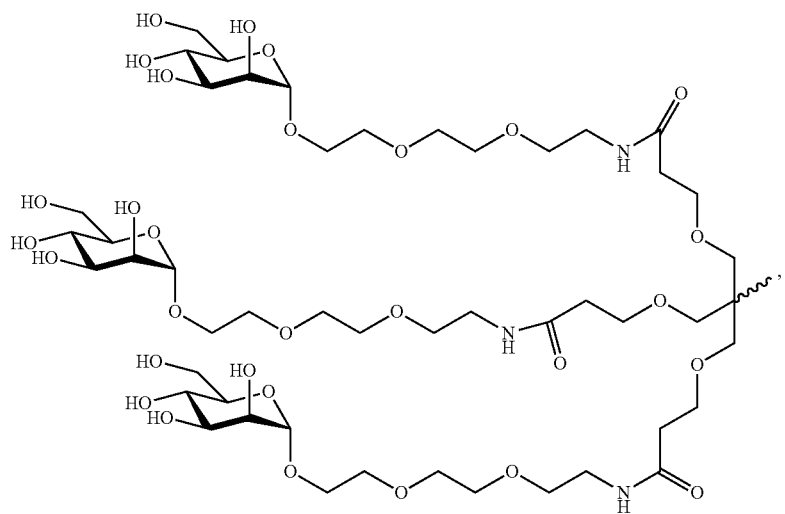

45
46
-continued
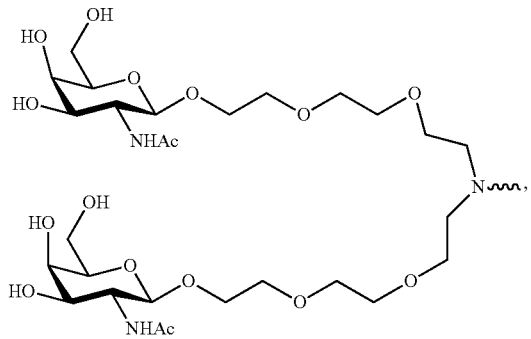
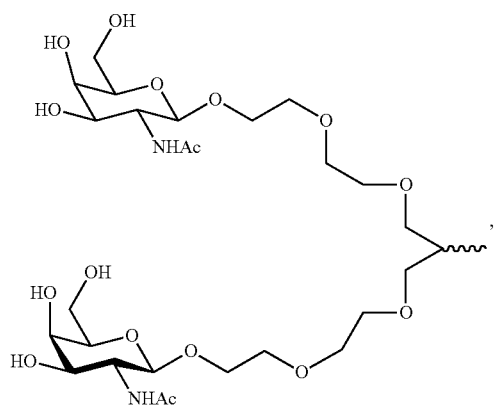
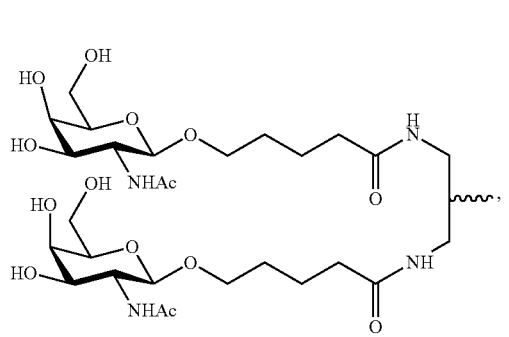
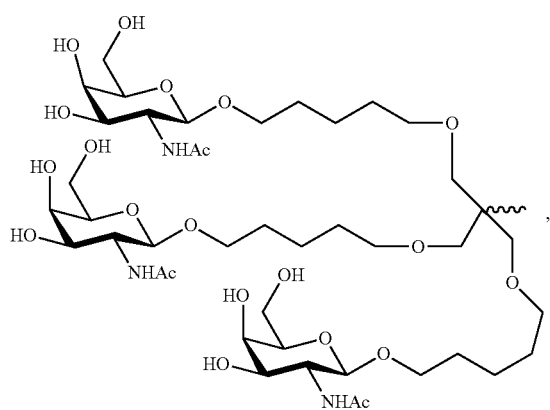
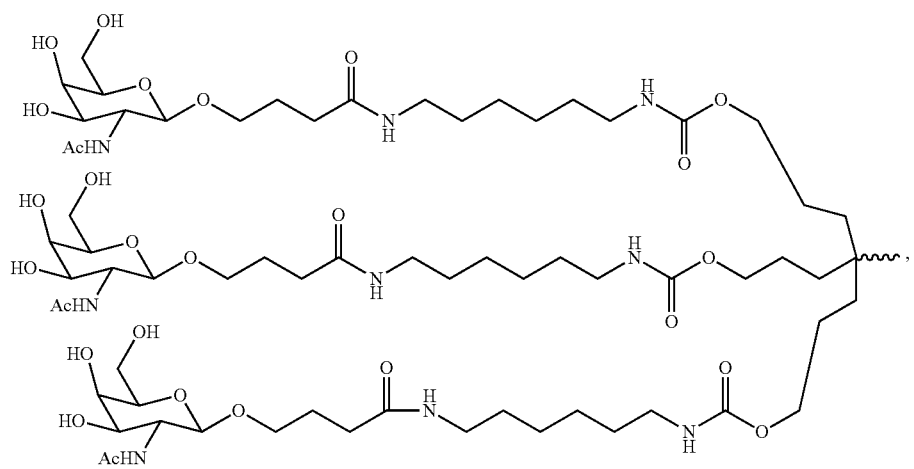

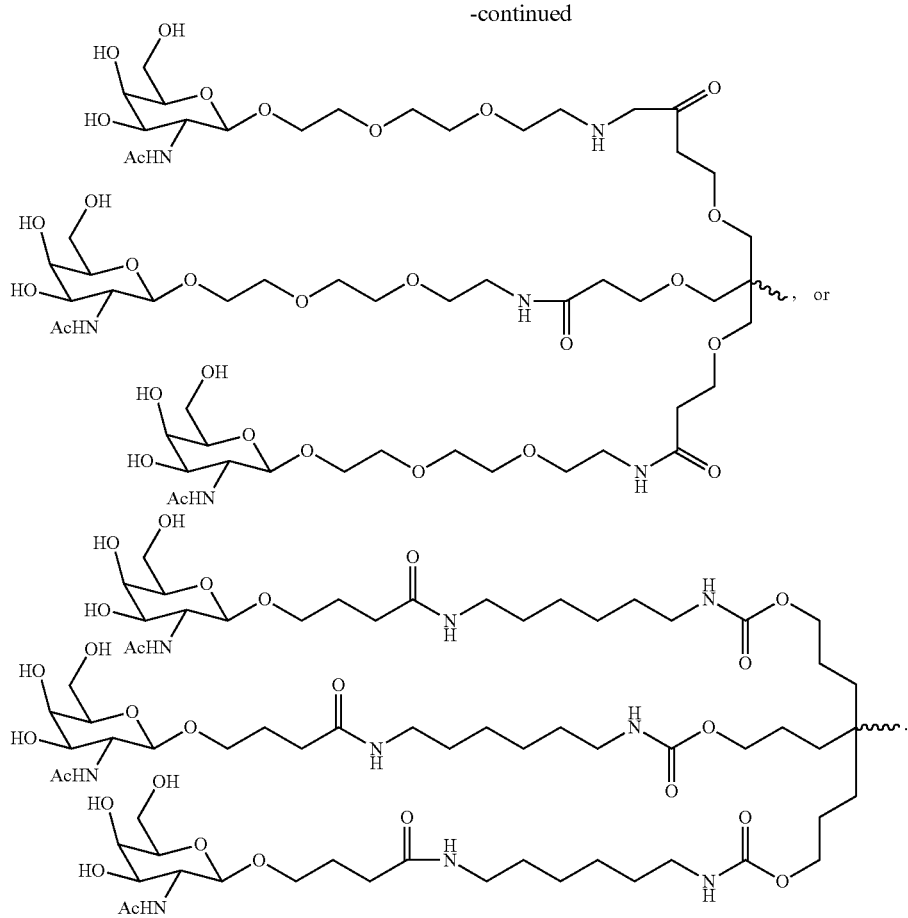

Definitions

As used herein, the terms "dsRNA", "siRNA", "RNAi agent", and "iRNA agent" re used interchangeably to agents that can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is a endogenous gene or a pathogen gene. In addition, RNAs other than mRNA, e.g., tRNAs, ad viral RNAs, can also be targeted.

An "iRNA agent" as used herein, is a RNA agent which can, or which can be cleaved into an RNA agent which can, down regulate the expression of a target gene, preferably an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent (e.g., dsRNA or siRNA). If the iRNA agent is a single strand it is particularly preferred that it include a 5' modification which includes one or more phosphate groups or one or more analogs of a phosphate group.

In one embodiment, iRNA agent can have any architecture. E.g., an iRNA agent can have an overhang structure, a hairpin, or other single strand structure, or a two-strand structure, as described herein.

iRNA agents include: molecules that are long enough to trigger the interferon response (which can be cleaved by Dicer (Bernstein et al. 2001. Nature, 409:363-366) and enter a RISC (RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed sRNA agents or shorter iRNA agents herein. "sRNA agent or shorter iRNA agent (siRNA)" as used herein, refers to an iRNA agent, e.g., a double stranded RNA agent or single strand agent, that is sufficiently short that it does not induce a deleterious interferon response in a human cell, e.g., it has a duplexed region of less than 60 but preferably less than 50, 40, or 30 nucleotide pairs. The sRNA agent, or a cleavage product thereof, can down regulate a target gene, e.g., by inducing RNAi with respect to a target RNA, preferably an endogenous or pathogen target RNA.

The term "single-stranded RNAi" or "ssRNAi" agent or molecule is an RNAi agent that is a single-stranded, nucleic acid-derived molecule having a nucleotide sequence that is partially, substantially, or perfectly complementary to a nucleotide sequence in a target nucleic acid molecule or a portion thereof. A second nucleotide sequence with which the single-stranded RNAi agent forms base-pairs is not present. A single-stranded RNAi molecule can further comprise a terminal phosphate group located at one or both of the terminal ends, such as a 5'-phosphate or a 5', 3'-diphosphate. An ssRNAi molecule/agent can include a miRNA or a miRNA mimetic. A single-stranded RNAi agent of the invention can be loaded into or otherwise associated with RISC and participate in gene silencing via an RNAi mechanism. A single-stranded RNAi molecule of the invention can comprise substitutions, chemically-modified nucleotides, and non-nucleotides. A single-stranded RNAi molecule of the invention can comprise one or more or all ribonucleotides. Certain embodiments of the invention include single-stranded RNAi molecules that comprise substitutions or modifications in the backbone, sugars, bases, or nucleosides.

The term "miRNA" or "microRNA" is used herein in accordance with its ordinary meaning in the art and refers to small, non-protein coding RNA molecules that are expressed in a diverse array of eukaryotes, including mammals, and are involved in RNA-based gene regulation. Mature, fully processed miRNAs are about 15 to about 30 nucleotides in length. A representative set of known, endogenous miRNA species is described in the publicly available miRBase sequence database, described in Griffith-Jones et al., Nucleic Acids Research, 2004, 32:D109-D111 and Griffith-Jones et al, Nucleic Acids Research, 2006, 34:D 140-D144, and accessible on the World Wide Web at the Wellcome Trust Sanger Institute website. The mature, fully-processed miR-NAs that are publicly available on the miRBase sequence database are each incorporated by reference herein. A representative set of miRNAs is also included herein.

The term "miRNA mimetic," as used herein, refers to a single-stranded RNA molecule that is a mimetic of a naturally-occurring miRNA in a cell. A miRNA mimetic is typically designed based on a corresponding, endogenous miRNA. A miRNA mimetic is capable of modulating the expression of a target mRNA that is also regulated by a corresponding, naturally-occurring miRNA. A single-stranded RNAi molecule of the present invention that is also a miRNA mimetic can be loaded into or otherwise associated with RISC and participates in gene silencing via an RNAi mechanism. A miRNA mimetic of the invention can comprise substitutions, chemically-modified nucleotides, and non-nucleotides. A miRNA mimetic of the invention can comprise one or more or all ribonucleotides. Certain embodiments of the invention include miRNA mimetics that comprise substitutions or modifications in the backbone, sugars, bases, or nucleosides. A naturally-occurring miRNA in a cell is referred to herein as "the corresponding miRNA," "the endogenous miRNA," or the "naturally-occurring miRNA." A single-stranded miRNA mimetic of the invention that is provided to a cell is also understood to target one or more target mRNAs that are also targeted by a corresponding, naturally-occurring miRNA. It is contemplated that a miRNA mimetic of the present invention introduced to a cell is capable of functioning as a naturally-occurring miRNA under appropriate conditions.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In one embodiment, a dsRNA agent is "sufficiently complementary" to a target RNA, e.g., a target mRNA, such that the dsRNA agent silences production of protein encoded by the target mRNA. In another embodiment, the dsRNA agent is "exactly complementary" to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA agent specifically discriminates a single-nucleotide difference. In this case, the dsRNA agent only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

The term "halo" refers to any radical of fluorine, chlorine, bromine or iodine. The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include trizolyl, tetrazolyl, piperazinyl, pyrrolidinyl, dioxanyl, morpholinyl, tetrahydrofuranyl, and the like.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)

(ORk)-O—, —O—P(O)(ORk)-S—, —S—P(OXORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—).

The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

Alternative Embodiments

In another embodiment, the invention relates to a dsRNA agent capable of inhibiting the expression of a target gene in vivo. The dsRNA agent comprises a sense strand and an antisense strand, each strand having 14 to 30 nucleotides. The sense strand contains at least one motif of three identical modifications on three consecutive nucleotides, where at least one of the motifs occurs at or near the cleavage site in the antisense strand. Every nucleotide in the sense strand and antisense strand has been modified. The modifications on sense strand and antisense strand each independently comprises at least two different modifications.

In another embodiment, the invention relates to a dsRNA agent capable of inhibiting the expression of a target gene in vivo. The dsRNA agent comprises a sense strand and an antisense strand, each strand having 14 to 30 nucleotides. The sense strand contains at least one motif of three identical modifications on three consecutive nucleotides, where at least one of the motifs occurs at or near the cleavage site in the antisense strand. The antisense strand contains at least one motif of three identical modifications on three consecutive nucleotides. The modification pattern of the antisense strand is shifted by one or more nucleotides relative to the modification pattern of the sense strand.

In another embodiment, the invention relates to a dsRNA agent capable of inhibiting the expression of a target gene in vivo. The dsRNA agent comprises a sense strand and an antisense strand, each strand having 14 to 30 nucleotides. The sense strand contains at least two motifs of three identical modifications on three consecutive nucleotides, when at least one of the motifs occurs at the cleavage site in the strand and at least one of the motifs occurs at another portion of the strand that is separated from the motif at the cleavage site by at least one nucleotide. The antisense strand contains at least one motif of three identical modifications on three consecutive nucleotides, where at least one of the motifs occurs at or near the cleavage site in the strand and at least one of the motifs occurs at another portion of the strand that is separated from the motif at or near cleavage site by at least one nucleotide.

In another embodiment, the invention relates to a dsRNA agent capable of inhibiting the expression of a target gene in vivo. The dsRNA agent comprises a sense strand and an antisense strand, each strand having 14 to 30 nucleotides. The sense strand contains at least two motifs of three identical modifications on three consecutive nucleotides, where at least one of the motifs occurs at the cleavage site in the strand and at least one of the motifs occurs at another portion of the strand that is separated from the motif at the cleavage site by at least one nucleotide. The antisense strand contains at least one motif of three identical modifications on three consecutive nucleotides, where at least one of the motifs occurs at or near the cleavage site in the strand and at least one of the motifs occurs at another portion of the strand that is separated from the motif at or near cleavage site by at least one nucleotide. The modification in the motif occurring at the cleavage site in the sense strand is different than the modification in the motif occurring at or near the cleavage site in the antisense strand. In another embodiment, the invention relates to a dsRNA agent capable of inhibiting the expression of a target gene in vivo. The dsRNA agent comprises a sense strand and an antisense strand, each strand having 12 to 30 nucleotides. The sense strand contains at least one motif of three 2'-F modifications on three consecutive nucleotides, where at least one of the motifs occurs at the cleavage site in the strand. The antisense strand contains at least one motif of three 2'-O-methyl modifications on three consecutive nucleotides.

The sense strand may further comprises one or more motifs of three identical modifications on three consecutive nucleotides, where the one or more additional motifs occur at another portion of the strand that is separated from the three 2'-F modifications at the cleavage site by at least one nucleotide. The antisense strand may further comprises one or more motifs of three identical modifications on three consecutive nucleotides, where the one or more additional motifs occur at another portion of the strand that is separated from the three 2'-O-methyl modifications by at least one nucleotide. At least one of the nucleotides having a 2'-F modification may form a base pair with one of the nucleotides having a 2'-O-methyl modification.

In one embodiment, the dsRNA of the invention is administered in buffer.

In one embodiment, siRNA compounds described herein can be formulated for administration to a subject. A formulated siRNA composition can assume a variety of states. In some examples, the composition is at least partially crystalline, uniformly crystalline, and/or anhydrous (e.g., less than 80, 50, 30, 20, or 100/water). In another example, the siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly.

A siRNA preparation can be formulated in combination with another agent, e.g., another therapeutic agent or an agent that stabilizes a siRNA, e.g., a protein that complexes with siRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the siRNA preparation includes another siNA compound, e.g., a second siRNA that can mediate RNAi with respect to a second gene, or with respect to the same gene. Still other preparation can include at least 3, 5, ten, twenty, fifty, or a hundred or more different siRNA species. Such siRNAs can mediate RNAi with respect to a similar number of different genes.

In one embodiment, the siRNA preparation includes at least a second therapeutic agent (e.g., an agent other than a RNA or a DNA). For example, a siRNA composition for the treatment of a viral disease, e.g., HIV, might include a known antiviral agent (e.g., a protease inhibitor or reverse transcriptase inhibitor). In another example, a siRNA com position for the treatment of a cancer might further comprise a chemotherapeutic agent.

Exemplary formulations are discussed below.

Liposomes.

For ease of exposition the formulations, compositions and methods in this section are discussed largely with regard to unmodified siRNA compounds. It may be understood, however, that these formulations, compositions and methods can be practiced with other siRNA compounds, e.g., modified siRNAs, and such practice is within the invention. An siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the siRNA composition. The lipophilic material isolates the aqueous interior from an aqueous exterior, which typically does not include the siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the siRNA are delivered into the cell where the siRNA can specifically bind to a target RNA and can mediate RNAi. In some cases the liposomes are also specifically targeted, e.g., to direct the siRNA to particular cell types.

A liposome containing a siRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The siRNA preparation is then added to the micelles that include the lipid component. The cationic groups on the lipid interact with the siRNA and condense around the siRNA to form a liposome. After condensation, the detergent is removed, e.g., by dialysis, to yield a liposomal preparation of siRNA.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Felgner, P. L. et al., *Proc. Natl. Acad. Sci., USA* 8:7413-7417, 1987; U.S. Pat. No. 4,897,355; U.S. Pat. No. 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; U.S. Pat. No. 5,171,678; WO 94/00569; WO 93/24640; WO 91/16024; Feigner, *J. Biol. Chem.* 269:2550, 1994; *Nabel, Proc. Natl. Acad. Sci.* 90:11307, 1993; *Nabel, Human Gene Ther.* 3:649, 1992; *Gershon, Biochem.* 32:7143, 1993; and Strauss *EMBO J.* 11:417, 1992.

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated siRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA (see, e.g., Feigner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoyl-phosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer siRNA, into the skin. In some implementations, liposomes are used for delivering siRNA to epidermal cells and also to enhance the penetration of siRNA into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2,405-410 and du Plessis et al., *Antiviral Research*, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with siRNA are useful for treating a dermatological disorder.

Liposomes that include siRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include siRNA can be delivered, for example, subcutaneously by infection in order to deliver siRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Surfactants.

For ease of exposition the formulations, compositions and methods in this section are discussed largely with regard to unmodified siRNA compounds. It may be understood, however, that these formulations, compositions and methods can be practiced with other siRNA compounds, e.g., modified siRNA compounds, and such practice is within the scope of the invention. Surfactants find wide application in formulations such as emulsions (including microemulsions) and liposomes (see above). siRNA (or a precursor, e.g., a larger dsiRNA which can be processed into a siRNA, or a DNA which encodes a siRNA or precursor) compositions can include a surfactant. In one embodiment, the siRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, N.Y., 1988, p. 285).

Micelles and Other Membranous Formulations.

For ease of exposition the micelles and other formulations, compositions and methods in this section are discussed largely with regard to unmodified siRNA compounds. It may be understood, however, that these micelles and other formulations, compositions and methods can be practiced with other siRNA compounds, e.g., modified siRNA compounds, and such practice is within the invention. The siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles.

For ease of exposition the particles, formulations, compositions and methods in this section are discussed largely with regard to modified siRNA compounds. It may be understood, however, that these particles, formulations, compositions and methods can be practiced with other siRNA compounds, e.g., unmodified siRNA compounds, and such practice is within the invention. In another embodiment, an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques.

Pharmaceutical Compositions

The iRNA agents of the invention may be formulated for pharmaceutical use. Pharmaceutically acceptable compositions comprise a therapeutically-effective amount of one or more of the the dsRNA agents in any of the preceding embodiments, taken alone or formulated together with one or more pharmaceutically acceptable carriers (additives), excipient and/or diluents.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Delivery using subcutaneous or intravenous methods can be particularly advantageous.

The phrase "therapeutically-effective amount" as used herein means that amount of a compound, material, or composition comprising a compound of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (I) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

iRNA agent preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The compounds according to the invention may be formulated for administration in any convenient way for use in human or veterinary medicine, by analogy with other pharmaceuticals.

The term "treatment" is intended to encompass also prophylaxis, therapy and cure. The patient receiving this treatment is any animal in need, including primates, in particular humans, and other mammals such as equines, cattle, swine and sheep; and poultry and pets in general.

Double-stranded RNAi agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen el al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA agent and one that produces a transcript that includes the bottom strand of a dsRNA agent. When the templates are transcribed, the dsRNA agent is produced, and processed into siRNA agent fragments that mediate gene silencing.

Routes of Delivery

A composition that includes an iRNA can be delivered to a subject by a variety of routes. Exemplary routes include: intravenous, subcutaneous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Dosage

In one aspect, the invention features a method of administering a dsRNA agent, e.g., a siRNA agent, to a subject (e.g., a human subject). The method includes administering a unit dose of the dsRNA agent, e.g., a siRNA agent, e.g., double stranded siRNA agent that (a) the double-stranded part is 14-30 nucleotides (nt) long, for example, 21-23 nt, (b) is complementary to a target RNA (e.g., an endogenous or pathogen target RNA), and, optionally, (c) includes at least one 3' overhang 1-5 nucleotide long. In one embodiment, the unit dose is less than 10 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an antiviral agent other than a dsRNA agent, e.g., other than a siRNA agent. In another embodiment, the subject has atherosclerosis and the effective dose of a dsRNA agent, e.g., a siRNA agent, is administered in combination with, e.g., after surgical intervention, e.g., angioplasty.

In one embodiment, a subject is administered an initial dose and one or more maintenance doses of a dsRNA agent, e.g., a siRNA agent, (e.g., a precursor, e.g., a larger dsRNA agent which can be processed into a siRNA agent, or a DNA which encodes a dsRNA agent, e.g., a siRNA agent, or precursor thereof). The maintenance dose or doses can be the same or lower than the initial dose, e.g., one-half less of the initial dose. A maintenance regimen can include treating the subject with a dose or doses ranging from 0.01 μg to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the composition includes a plurality of dsRNA agent species. In another embodiment, the dsRNA agent species has sequences that are non-overlapping and non-adjacent to another species with respect to a naturally occurring target sequence. In another embodiment, the plurality of dsRNA agent species is specific for different naturally occurring target genes. In another embodiment, the dsRNA agent is allele specific.

The inventors have discovered that dsRNA agents described herein can be administered to mammals, particularly large mammals such as nonhuman primates or humans in a number of ways.

In one embodiment, the administration of the dsRNA agent, e.g., a siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of dsRNA agents described herein Methods of Inhibiting Expression of the Target Gene Embodiments of the invention also relate to methods for inhibiting the expression of a target gene. The method comprises the step of administering the dsRNA agents in any of the preceding embodiments, in an amount sufficient to inhibit expression of the target gene.

Another aspect the invention relates to a method of modulating the expression of a target gene in a cell, comprising providing to said cell a dsRNA agent of this invention. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erkl/2 gene, PCNA(p21) gene, MYB gene, JUN gene, FOS gene, BCL-2 gene, hepciden, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase 1 gene, topoisomerase II alpha gene, mutations in the p73 gene, mutations in the p21(WAF1/CIP1) gene, mutations in the p27(KIP1) gene, mutations in the PPMID gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

The invention is further illustrated by the following examples, which should not be construed as further limiting. The contents of all references, pending patent applications and published patents, cited throughout this application are hereby expressly incorporated by reference.

EXAMPLES

Example 1. Synthesis of 4'-Modified Nucleoside Building Blocks

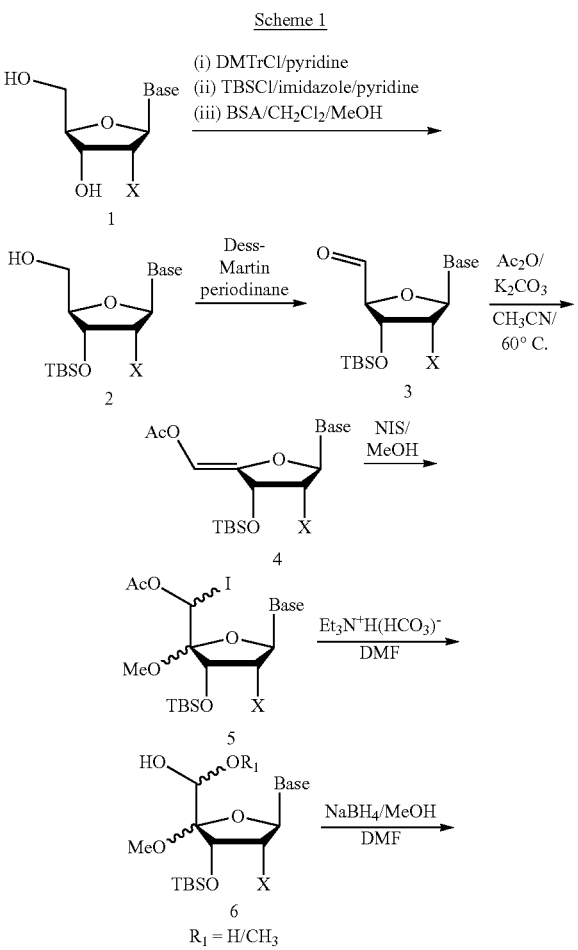

Scheme 1

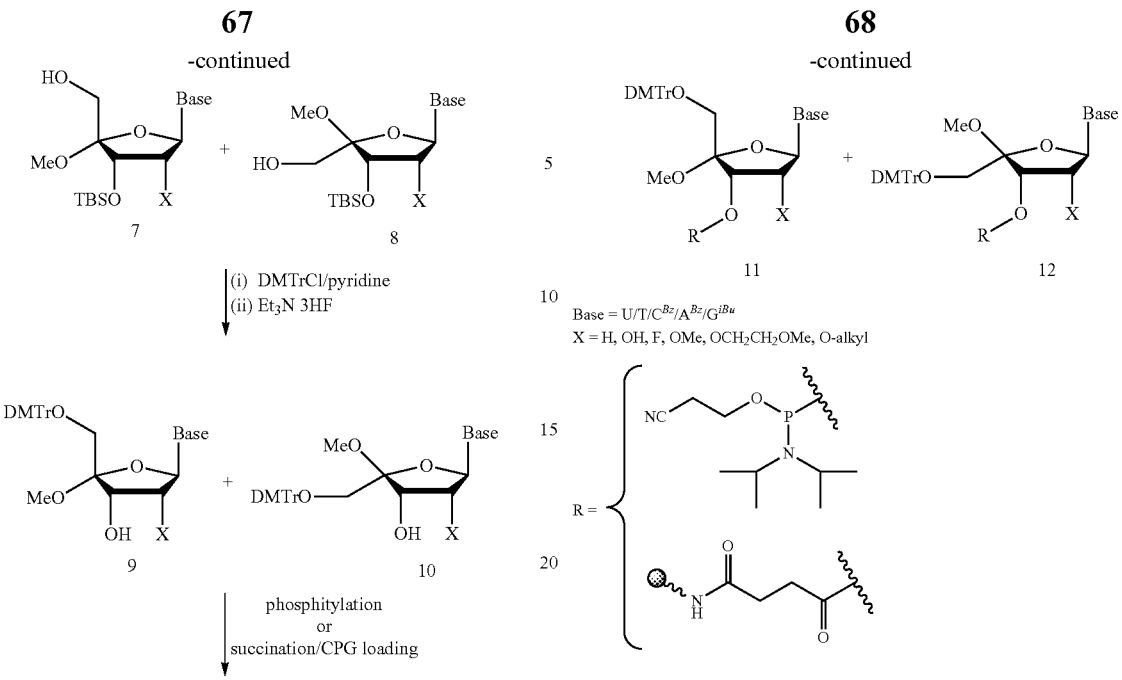
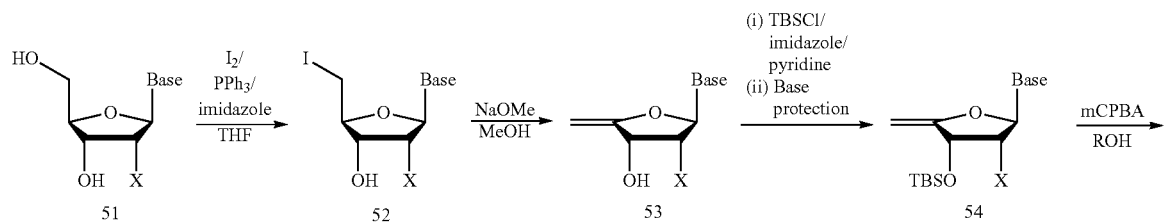
Scheme 2. General synthesis of 4'-modified nucleoside
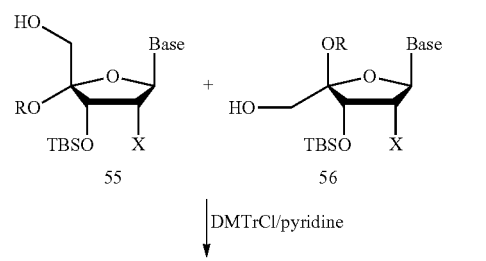
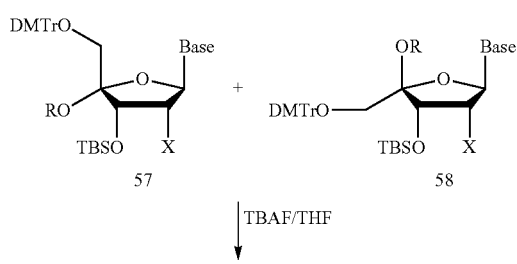

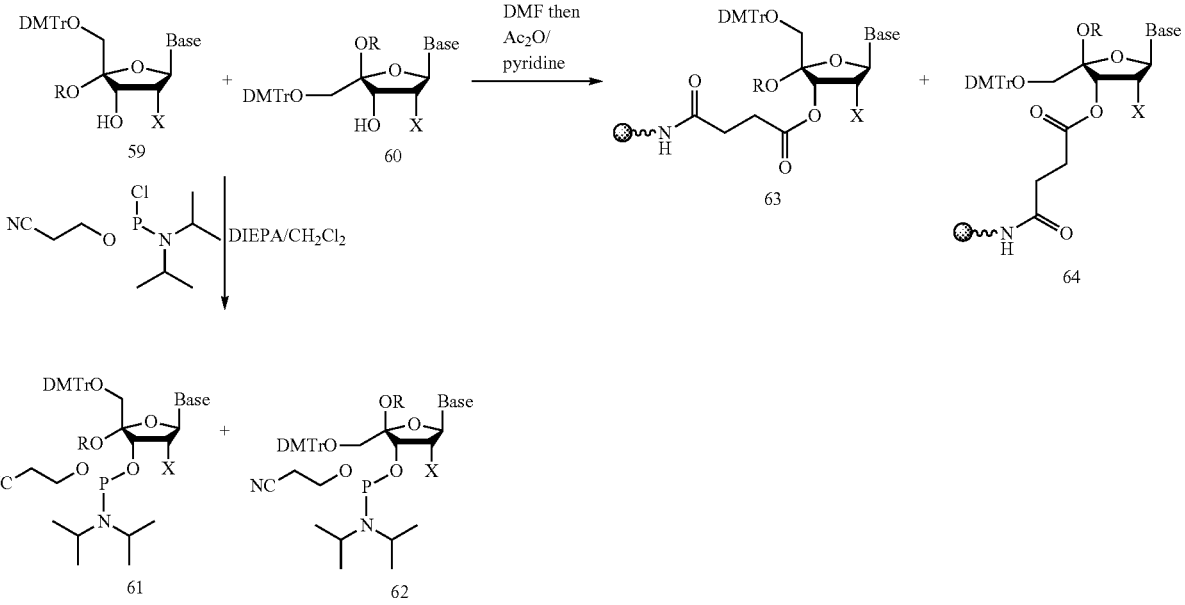
Base: U/T/C/A/G or $C^{Bz}/A^{Bz}/G^{iBu}$
R: Me, Et, MeOCH$_2$CH$_2$, alkyl, etc
X: H, OH, OMe, F, OCH$_2$CH$_2$OMe, O-alkyl, etc
Example 2. Synthesis of 4'-OMe Nucleoside Building Blocks
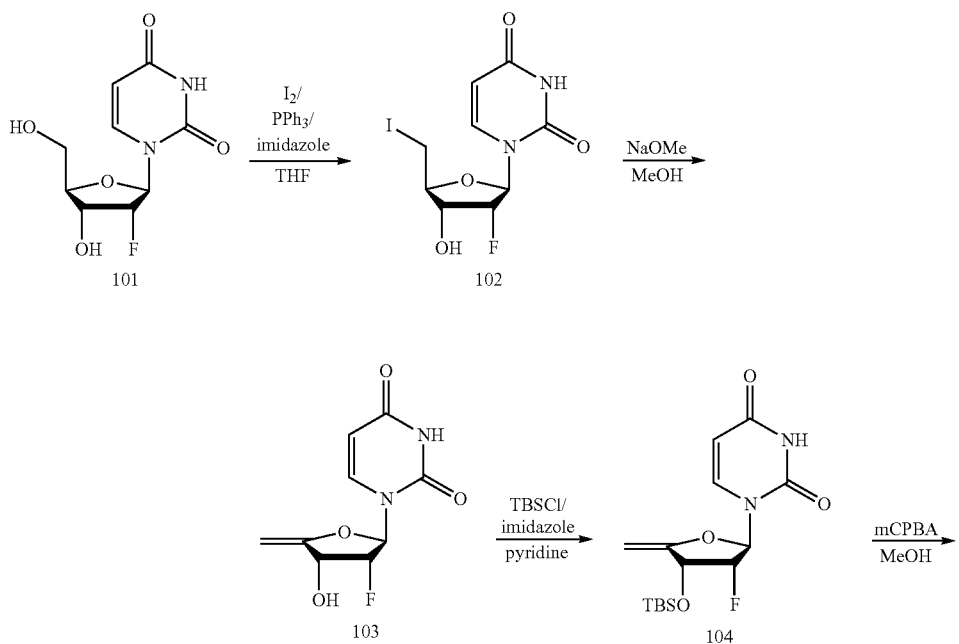

-continued
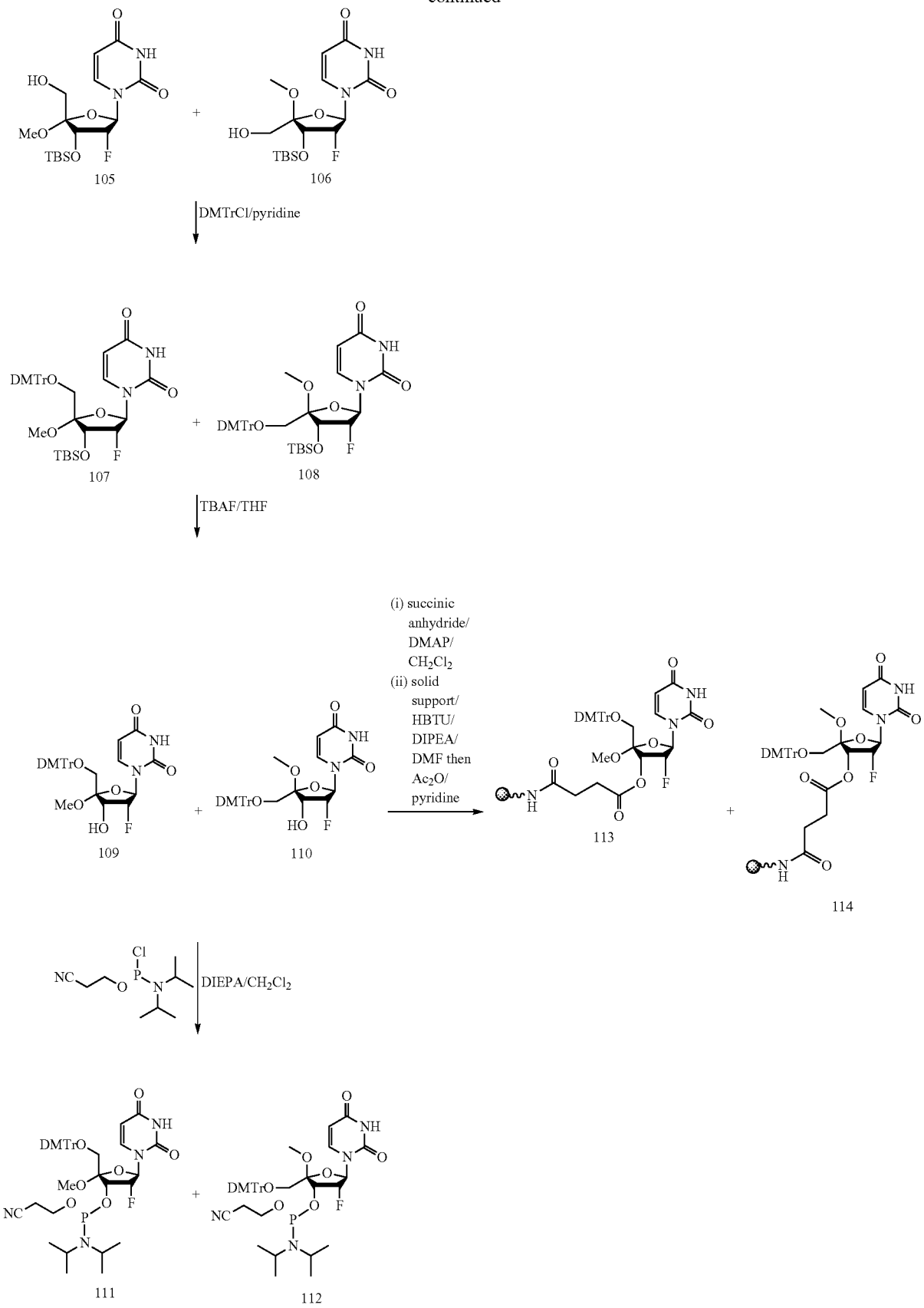

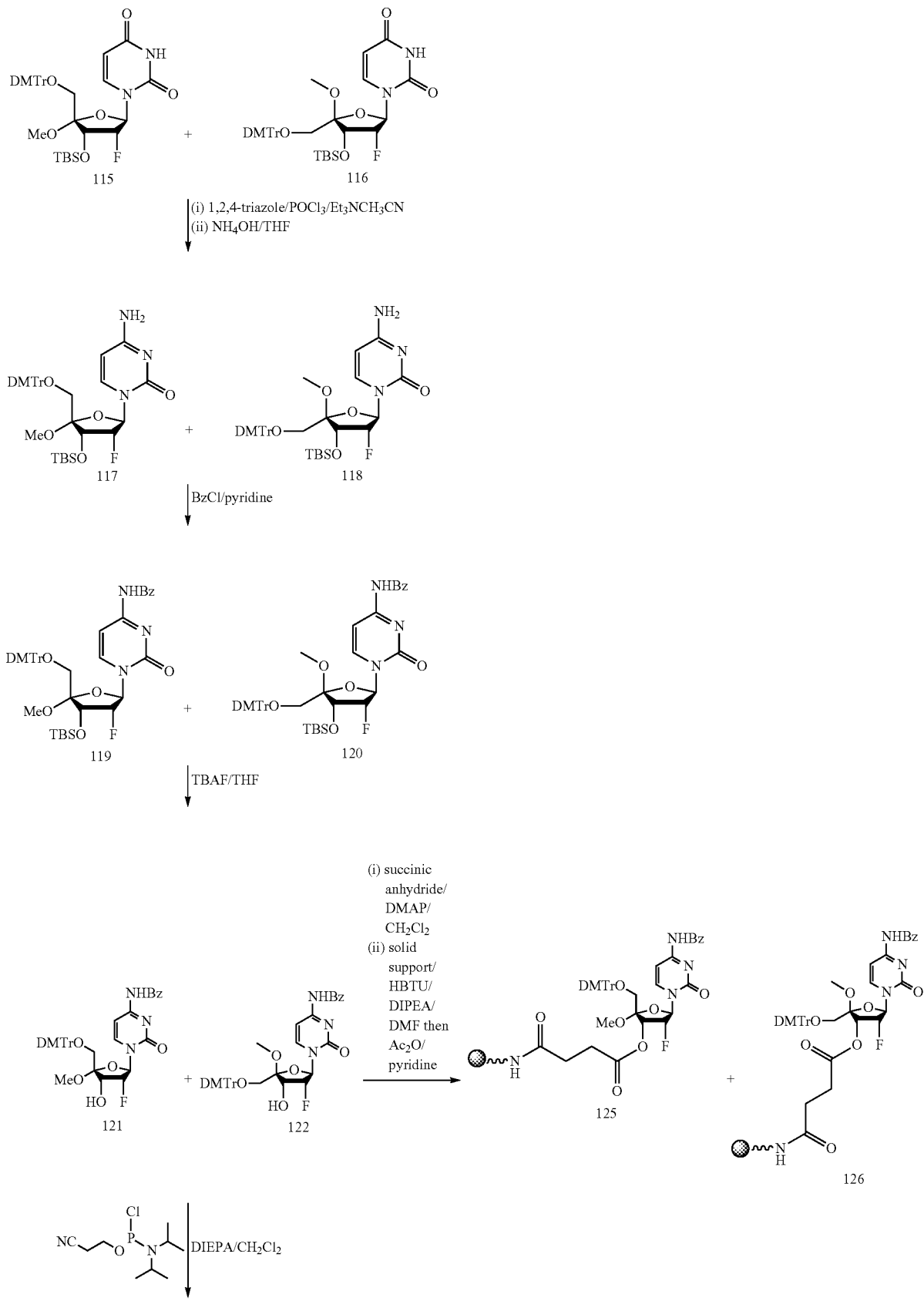
Scheme 4. 4'-OMe 2'-fluorocytidine building block synthesis

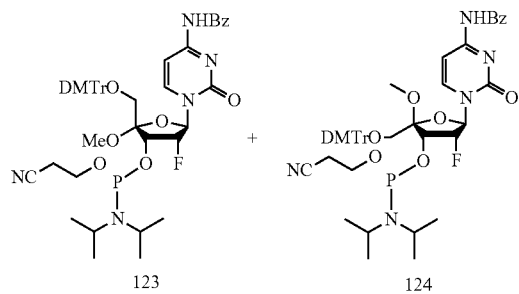
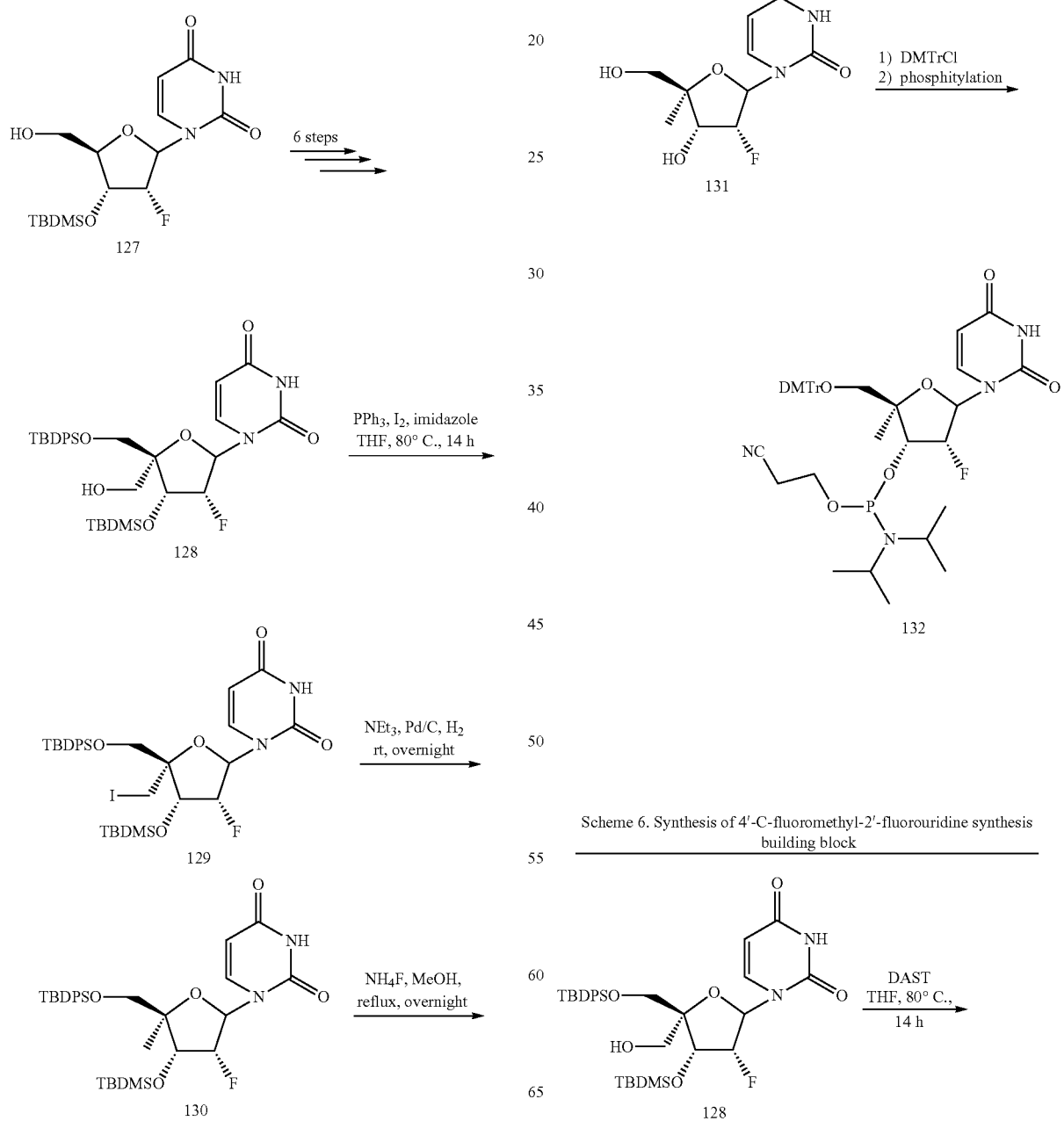

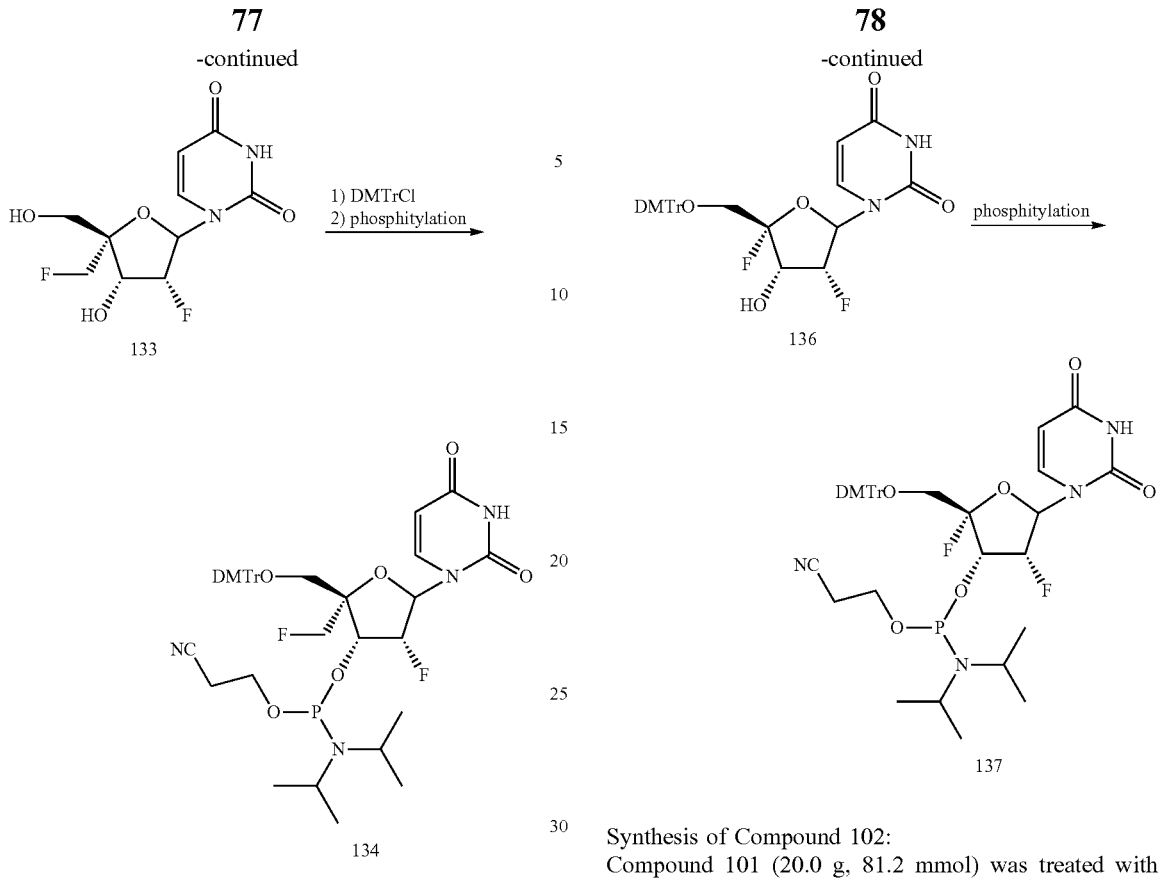

Scheme 7. Synthesis of 4'-fluoro-2'-fluorouridine synthesis building block

Synthesis of Compound 102:

Compound 101 (20.0 g, 81.2 mmol) was treated with PPh$_3$ (31.9 g, 121.8 mmol), imidazole (13.8 g, 203 mmol) and I$_2$ (30.9 g, 121.8 mmol) in THF (400 mL) for 18 h. Aqueous work-up then column chromatography gave compound 102 (27.9 g, 78.2 mmol, 96%). Molecular weight for C$_9$H$_{11}$FIN$_2$O$_4$(M+H)$^+$ Calc. 355.9669. Found 357.0.

Synthesis of Compound 103:

Compound 102 (400 mg, 1.12 mmol) was treated with NaOMe (25 wt % solution in MeOH, 1.28 mL, 5.60 mmol) in MeOH (7 mL) at 65° C. for 5 h. Silica gel column purification gave compound 103 (162 mg, 0.710 mmol, 63%). Molecular weight for C$_9$H$_{10}$FN$_2$O$_4$(M+H)$^+$ Calc 229.0625. Found 229.1.

Synthesis of Compound 104:

Compound 103 (230 mg, 1.01 mmol) was treated with TBSCl (229 mg, 1.52 mmol) and imidazole (206 mg, 3.03 mmol) in pyridine (3 mL) at r.t overnight. Aqueous work-up then column chromatography gave compound 104 (300 mg, 0.876 mmol, 87%). $^1$H NMR (400 MHz, DMSO-d$_6$) δ 11.51 (s, 1H), 7.63 (d, J=8.1 Hz, 1H), 6.05 (dd, J=19.4, 1.9 Hz, 1H), 5.68 (d, J=8.0 Hz, 1H), 5.38 (ddd, J=52.9, 5.1, 1.9 Hz, 1H), 5.14-4.96 (m, 1H), 4.50 (s, 1H) 4.20 (s, 1H), 0.90 (s, 9H), 0.14 (d, J=7.0 Hz, 6H).

Synthesis of Compound 105/106:

Compound 104 (290 mg, 0.847 mmol) was treated with mCPBA (390 mg, 1.69 mmol) in MeOH (10 mL) overnight. Aqueous work-up then column chromatography gave compound 105 (175 mg, 0.448 mmol, 53%) and compound 106 (57 mg, 0.146 mmol, 17%). compound 105: $^1$H NMR (500 MHz, DMSO-d$_6$) δ 11.43 (s, 1H), 7.79 (d, J=8.1 Hz, 1H), 6.04 (dd, J=18.2, 2.0 Hz, 1H), 5.66 (d, J=8.1 Hz, 1H), 5.30 (t, J=5.4 Hz, 1H), 5.12 (ddd, J=54.2, 5.8, 2.1 Hz, 1H), 4.53 (dd, J=20.5, 5.8 Hz, 1H), 3.67 (dd, J=11.7, 5.0 Hz, 1H), 3.39 (dd, J=11.8, 5.7 Hz, 1H), 3.30 (s, 3H), 0.89 (s, 9H), 0.10 (d, J=1.3 Hz, 6H).

Synthesis of Compound 107:

Compound 105 (165 mg, 0.423 mmol) was treated with DMTrCl (215 mg, 0.635 mmol) in pyridine (2 mL) for 14 h. Aqueous work-up then column chromatography gave compound 107 (262 mg, 0.378 mmol, 89%). Molecular weight for $C_{37}H_{45}FN_2NaO_8Si$ $(M+Na)^+$ Calc. 715.2827. Found 714.9.

Synthesis of Compound 109:

Compound 107 (7.10 g, 10.2 mmol) was treated with 1 M n-TBAF (16 mL, 16 mmol) in THF (50 mL) at r.t for 2 h. The solvent was removed and the residue was purified by silica gel column chromatography to give compound 109 (4.0 g, 6.91 mmol, 68%). Molecular weight for $C_{31}H_{30}FN_2O_8$ $(M-H)^-$ Calc. 577.1986. Found 577.0.

Synthesis of Compound 111/112:

Standard phosphitylation of compound 109/110 using 2-cyanoethyl N,N-diisopropylchlorophosphoramidite and DIPEA in $CH_2Cl_2$ gives compound 111/112.

Synthesis of Compound 113/114:

Standard succination of compound 109/110 using succinic anhydride and DMAP in $CH_2Cl_2$ followed by CPG loading using HBTU and DIPEA in DMF gives compound 113/114.

Synthesis of compound 117: Compound 115 (5.80 mg, 8.37 mmol) was treated with 1,2,4-triazole (5.78 g, 83.7 mmol) and $POCl_3$ (1.95 mL, 20.9 mmol) in $Et_3N$ (14 mL) and $CH_3CN$ (94 mL). Aqueous work-up gave crude material. This material was treated with $NH_4OH$ (20 mL) in THF (80 mL) overnight. The solvent was removed and the residue was purified by silica gel column chromatography to give compound 117 (4.71 g, 6.79 mmol, 81%). Molecular weight for $C_{37}H_{46}FN_3NaO_7Si$ $(M+Na)^+$ Calc. 714.2987. Found 714.0.

Synthesis of Compound 119:

Compound 117 (4.70 g, 6.79 mmol) was treated with DMTrCl (1.02 mL, 8.83 mmol) in pyridine (40 mL) for 14 h. Aqueous work-up then column chromatography gave compound 119 (4.41 g, 5.54 mmol, 82%). Molecular weight for $C_{44}H_{51}FN_3O_8Si$ $(M+H)^+$ Calc. 796.3429. Found 796.0.

Synthesis of Compound 121:

Compound 119 (4.35 g, 5.47 mmol) was treated with 1 M n-TBAF (6 mL, 6 mmol) in THF (40 mL) at r.t for 48 h. The solvent was removed and the residue was purified by silica gel column chromatography to give compound 121 (3.24 g, 4.75 mmol, 87%). Molecular weight for $C_{38}H_{37}FN_3O_8(M+H)^+$ Calc. 682.2565. Found 682.0.

Synthesis of Compound 123/124:

Standard phosphitylation of compound 121/122 using 2-cyanoethyl N,N-diisopropylchlorophosphoramidite and DIPEA in $CH_2Cl_2$ gives compound 123/124.

Synthesis of Compound 125/126:

Standard succination of compound 121/122 using succinic anhydride and DMAP in $CH_2Cl_2$ followed by CPG loading using HBTU and DIPEA in DMF gives compound 125/126.

Synthesis of Compound 128:

Compound 128 is prepared in 6 steps, starting from compound 127, according to the procedures described in the patent application WO2013142525.

Synthesis of Compound 129:

Compound 129 is prepared from compound 128, according to the procedures described in the patent application WO2013142525.

Synthesis of Compound 130:

Compound 130 is prepared from compound 129, according to the procedures described in the patent application WO2013142525.

Synthesis of Compound 131:

Compound 131 is prepared from compound 130, according to the procedures described in the patent application WO2013142525.

Synthesis of Compound 132:

Compound 132 is prepared from compound 131, in two steps: 1) Nucleoside 131 is dissolved in anhydrous pyridine, 1.1 equivalents of DMTrCl are added and the mixture is stirred overnight. The reaction is worked up and the crude compound is purified by silica gel flash chromatography; 2) Standard phosphitylation of the resulting nucleoside using 2-cyanoethyl N,N-diisopropylchlorophosphoramidite and DIPEA in $CH_2Cl_2$ gives compound 132.

Synthesis of Compound 133:

Compound 128 is dissolved in anhydrous THF and 3 equivalents of diethylaminosulfur trifluoride (DAST) are added and the mixture is stirred for 14 hours at 80° C. The reaction is worked up and the crude compound is purified by silica gel flash chromatography to yield compound 133.

Synthesis of Compound 134:

Compound 134 is prepared from compound 133, in two steps: 1) Nucleoside 133 is dissolved in anhydrous pyridine, 1.1 equivalents of DMTrCl are added and the mixture is stirred overnight. The reaction is worked up and the crude compound is purified by silica gel flash chromatography; 2) Standard phosphitylation of the resulting nucleoside using 2-cyanoethyl N,N-diisopropylchlorophosphoramidite and DIPEA in $CH_2Cl_2$ gives compound 134.

Synthesis of Compound 135:

Compound 135 is prepared from compound 101, according to the procedures described in the article by Martinez-Montero et al., *J. Org. Chem.*, 2014, 79 (12), pp 5627.

Synthesis of Compound 137:

Compound 137 is prepared from compound 135, in two steps: 1) Nucleoside 135 is dissolved in anhydrous pyridine, 1.1 equivalents of DMTrCl are added and the mixture is stirred overnight. The reaction is worked up and the crude compound is purified by silica gel flash chromatography yielding pure compound 136; 2) Standard phosphitylation of 136 using 2-cyanoethyl N,N-diisopropylchlorophosphoramidite and DIPEA in $CH_2Cl_2$ gives compound 137.

Synthesis of 4'- and 5'-siRNA-Ligand Conjugates Through 4'-Modified Nucleotide Analogs A series of siRNA-Ligand conjugates using the 4'-modified nucleotide analogs described here are synthesized using various conjugation approaches, such as post-synthetic conjugations through peptide coupling, disulfide bridge or "click"-chemistry techniques. The ligand (L) can also be introduced at the monomer building block stage. The ligand (L) is a monosaccharide (such as GalNAc), disaccharide, trisaccharide, tetrasaccharide, oligosaccharide, or polysaccharide; peptide, oligopeptide, RGD peptide, peptidoid; folate; cholesterol, lipid or heterocycle. These siRNA-Ligand conjugates are synthesized according to the procedures described by Nair et al., *J. Am. Chem. Soc.*, 2014, 136 (49), pp 16958.

Example 3. Solid-Phase Synthesis of Modified Oligonucleotides

RNA and modified RNA oligonucleotides bearing the 4'-modified nucleoside described here were synthesized on an ABI 394 DNA/RNA synthesizer using standard phosphoramidite chemistry with commercially available 5'-O-(4, 4'-dimethoxytrityl)-3'-O-(2-cyanoethyl-N,N-diisopropyl)

phosphoramidite monomers of uridine (U), 4-N-acetylcytidine ($C^{Ac}$), 6-N-benzoyladenosine ($A^{Bz}$) and 2-N-isobutyrylguanosine ($G^{iBu}$) with 2'-O-t-butyldimethylsilyl protected phosphoramidites, 2'-fluoro substituted phosphoramidites, 2'-O-methyl phosphoramidites and the 4'-modified nucleoside building blocks shown here. After synthesis, a small portion of the oligonucleotide-bound CPG was treated with 100 μL of methylamine solution (40 wt % in water, Aldrich) in a microtube (1 mL) at 65° C. for 10 min or concentrated ammonium hydroxide (30% wt in water, JTBaker) at 55° C. for 8 hours. The mixture was cooled on dry ice for 5 min and the solid suspension was spun down. The supernatant (80 μL) was decanted into another microtube and, if necessary for 2'-O-t-butyldimethylsilyl deprotection, heated with 120 μL of TEA-3HF (Lancaster Synthesis, Inc.) at 65° C. for 12 min. The purity of crude oligonucleotide was analyzed by RP-HPLC or IEX-HPLC and the mass was confirmed by LC-MS experiments.

Example 4. In Vitro Evaluation of the Modified siRNAs

Cells that were transfected in step 1 were split or fed one day prior to beginning the protocol. For each cell line, the number of cells needed for transfection, to reach 70-90% confluence 24 hours after transfection, was determined prior to the start of the experiment.

Step 1—Reverse Transfection 1.1 For a 10 nM single dose screen, each siRNA was diluted to 200 nM in 1×PBS so that 5 μl can be transfected into 100 μl of cells to give a final siRNA concentration of 10 nM in the well. Serially dilute 1:6 for a total of eight concentrations.

1.2 To each well of a 96 well plate, 5 μl of the 200 nM siRNA solution were added.

1.3 Cells were removed from the incubator; media was aspirated and rinsed with 0.25% trypsin to remove any remaining media, which may inactivate the trypsin.

1.4 For a 75 $cm^2$ culture flask, cells were released by adding 3 ml of 0.25% trypsin and incubated at 37° C. until cells floated, about 5 minutes.

1.5 To inactivate the trypsin, 27 ml of complete media without antibiotics was added, as appropriate for the cell type.

1.6 Cells were pipeted into a 50 ml conical tube and centrifuged for 3 min at 1200 RPM.

1.7 Media was removed from cells and replaced with 5-10 ml of complete media without antibiotics.

1.8 Cells were counted to determine the total volume of cells that was needed for the 96-well plate. At a density of $2\times10^4$ cells per well, approximately $2\times10^6$ cells were needed per plate.

1.9 The cell suspension was prepared by resuspending the cells in complete media such that 80 μl of media contained $2\times10^4$ cells.

1.10 In a separate reservoir, 0.2 μl Lipofectamine RNAiMAX was mixed with 14.8 μl of Opti-MEM for each well that was transfected plus an appropriate amount of overage to account for dead volume (~10%). (For each 96-well plate that comes to 22 μl of RNAiMAX and 1.56 mls of Opti-MEM.)

1.11 The mixture was immediately distributed to the 96 well plates containing the siRNA and incubated for 20 min. at room temperature.

1.12 To each well, 80 μl of the cell suspension was added.

1.13 The plates were incubated for 24 hours at the appropriate temperature and $CO_2$ concentration for the cell line being used.

Step 2. RNA Isolation Using MagMax Magnetic Bead Purification.

2.1 The solutions below were prepared for each 96 well plate of RNA to be purified:
Added 6 ml isopropanol to Wash Solution 1.
Added 44 ml ethanol to Wash Solution 2.
Added 6 ml isopropanol to RNA Rebinding Concentrate.
Added 9 ml isopropanol to Lysis Binding Solution Concentrate.
Added 110 μl of Turbo DNase to 5.4 ml of MagMax Turbo DNase Buffer and was stored on ice until use.

2.2 Beads were vortexed for 15 sec. In a sterile reservoir 1.1 ml of beads was mixed with 1.1 ml of Lysis/Binding Enhancer for each 96 well plate of cells.

2.3 20 μl of the bead mixture was distributed to each well of a round bottom plate.

2.4 Cell culture media was removed from cells that were transfected in step 1.

2.5 140 μl Lysis/Binding solution was added to the cells and shaken for 1 min at 650 RPM in an eppendorf plate shaker.

2.6 The 140 μl of cell lysate was added to the beads in the round bottom plate and shaken for 5 minutes at 650 RPM to capture the RNA. The round bottom plate was placed on a magnetic ring stand for 1 minute.

2.7 With the plate on the magnetic ring stand the lysis mixture was removed using a 12 channel micropipette or by gently inverting the plate.

2.8 150 μl of Wash Solution 1 was added and shaken for 1 min at 650 RPM. The plate was placed on a magnetic stand for 1 min. then the wash solution was removed.

2.9 150 μl of Wash Solution 2 was added and shaken for 1 min at 650 RPM. The plate was placed on a magnetic stand for 1 min then the wash solution was removed.

2.10 50 μl DNase mix was added to each well and shaken at 650 RPM for 15 minutes.

2.11 100 μl RNA Rebinding Solution was added to each well and shaken for 3 min at 650 RPM to recapture the RNA. The plate was placed on a magnetic ring stand for 1 min and the Rebinding Solution was removed.

2.12 150 μl of Wash solution 2 was added and shaken for 1 min at 650 RPM. The plate was placed on a magnetic ring stand for 1 min and then the wash solution was removed.

2.13 To make sure as much liquid is removed as possible before drying; the plate was place on the shaker for 10 seconds at 650 RPM to gather any remaining liquid at the bottom of the well. The plate was placed on a magnetic ring stand and the remaining liquid was removed with a 12 channel micropipette.

2.14 The beads were dried by shaking at 650 RPM for 2-5 min.

2.15 50 μl of RNase free water was added to the dried beads and shaken for 3 min to elute the RNA.

2.16 The plate was placed on a magnetic stand for 1 min then 45 μl of eluted RNA were carefully aspirated without disturbing the magnetic beads. The eluted RNA was placed in a new plate.

2.17 The concentration of RNA was measured from a subset of wells to ensure that recovery was adequate and consistent across the plate using a spectrophotometer or Nanodrop.

Step 3. cDNA Synthesis
Overview

In this step cDNA was generated from the RNA that was isolated in the step 2.

The cDNA served as the template for the qPCR in step 4.

3.1 For each RNA sample a master mix containing 1 µl of 10× buffer, 0.4 µl of 25×dNTPs, 1 µl of random primers, 0.5 µl of Reverse transcriptase and 0.5 µl of RNase inhibitor and 1.6 µl of H₂O was prepared. (For each 96-well plate that comes to 100 µl of 10× buffer, 40 µl of 25×dNTPs, 100 µl of random primers, 50 µl of Reverse transcriptase, 50 µl of RNase inhibitor, and 160 µl of H₂O.)

3.2 5 µl of master mix was distributed to each well of a 96 or 384 well plate.

3.3 5 µl of total RNA isolated in step 2 was added to each well, maintaining the plate map that has been established during transfection.

3.4 The plate was centrifuged for 30 sec at 2,000 RPM in a centrifuge equipped to spin 96 well plates.

3.5 The following steps were cycled through using a thermocycler: 25 OC for 10 min, 37° C. for 120 min, 85° C. for 5 min, and hold at 4° C.

Step 4 qPCR 4.1 A qPCR master mix containing 0.5 µl of 20× gene specific TaqMan probe, 0.5 µl of 20× endogenous control TaqMan probe with 5 µl of Roche qPCR master mix and 3 µl of water for each qPCR reaction plus an appropriate amount of overage to account for dead volume was prepared. (for a 96-well plate that comes to 53 µl of 20× gene specific TaqMan probe, 53 µl of 20× endogenous control TaqMan probe with 530 µl of Roche qPCR master mix and 330 µl of water.)

4.2 8 µl of master mix was distributed to 96 or 384 well qPCR plates and centrifuged at 2,000 RPM for 15 sec to pool master mix at the bottom of the well.

4.3 2 µl of cDNA was added to the master mix. Replicate qPCR reactions were run on the same plate, or on separate plates. Plates were sealed and centrifuged at 2,000 RPM for 15 seconds.

4.4 The qPCR reactions were run using a method that can detect fluorescence from both VIC and FAM. On a Roche LightCycler 480 the standard—Dual Color Hydrolysis Probe/UPL Probe program was used.

In vitro RNAi silencing data was analyzed in Graph Pad and the IC$_{50}$ curves were generated and the data is represented in Table 1.

TABLE 1

In vitro potency of 4'-modified siRNAs: Ufo = 4'-methoxy-2'-deoxy-2'-fluoro-uridine; dTo = 4'-methoxy-2'-deoxy-thymidine. Nf = 2'-deoxy-2'-fluoro-nucleotide. n = 2'-O-methyl-nucleotide. dT = 2'-deoxy-thymidine, s = phosphorothioate. L96 = GalNAc ligand.

| Duplex ID | Sense ID | Sense (5' to 3') | SEQ ID NO: | AS ID | Antisense (5' to 3') | SEQ ID NO: | IC50 (nM) |
|---|---|---|---|---|---|---|---|
| AD-1 | S-1 | UfsgsAfcAfaAfaUfAfAfcUfcAfcUfaUfaAfL96 | 5 | AS-1 | usUfsaUfaGfuGfaGfuuaUfuUfuGfuCfasasu | 23 | 0.01 |
| AD-2 | S-2 | UfsgsAfcAfaAfaUfAfAfcUfcAfcUfaUfaAfL96 | 6 | AS-2 | usUfsaUfaGfuGfaGfuua(Ufo)uUfuGfuCfasasu | 24 | 7.22 |
| AD-3 | S-3 | UfsgsAfcAfaAfaUfAfAfcUfcAfcUfaUfaAfL96 | 7 | AS-3 | us(Ufos)aUfaGfuGfaGfuua(Ufo)uUfuGfuCfasasu | 25 | na |
| AD-4 | S-4 | UfsgsAfcAfaAfaUfAfAfcUfcAfcUfaUfaAfL96 | 8 | AS-4 | usUfsa(Ufo)aGfuGfaGfuuaUfu(Ufo)uGfuCfasasu | 26 | 0.34 |
| AD-5 | S-5 | usgsacaaaauAfAfcucacuauaaL96 | 9 | AS-5 | usUfsa(Ufo)aGfuGfaGfuuaUfu(Ufo)uGfuCfasasu | 27 | 0.84 |
| AD-6 | S-6 | UfsgsAfcAfaAfaUfAfAfcUfcAfcUfaUfaAfL96 | 10 | AS-6 | usUfsaUfaGfuGfaGfuua(dTo)uUfuGfuCfasasu | 28 | na |
| AD-7 | S-7 | UfsgsAfcAfaAfaUfAfAfcUfcAfcUfaUfaAfL96 | 11 | AS-7 | us(dTos)aUfaGfuGfaGfuuaUfu(dTo)uGfuCfasasu | 29 | 1.34 |
| AD-8 | S-8 | UfsgsAfcAfaAfaUfAfAfcUfcAfcUfaUfaAfL96 | 12 | AS-8 | usUfsa(dTo)aGfuGfaGfuuaUfu(dTo)uGfuCfasasu | 30 | na |
| AD-9 | S-9 | usgsacaaaauAfAfcucacuauaaL96 | 13 | AS-9 | usUfsa(dTo)aGfuGfaGfuuaUfu(dTo)uGfuCfasasu | 31 | na |
| AD-10 | S-I0 | AfsasCfaGfuGfuUfCfUfuGfcUfcUfaUfaAfL96 | 14 | AS-10 | usUfsaUfaGfaGfcAfagaAfcAfcUfgUfususu | 32 | 0.02 |
| AD-11 | S-11 | AfsasCfaGfuGfuUfCf(Ufo)uGfcUfcUfaUfaAfL96 | 15 | AS-11 | usUfsaUfaGfaGfcAfagaAfcAfcUfgUfususu | 33 | 0.04 |
| AD-12 | S-12 | AfsasCfaGfuGfuUfCfUfuGfcUfcUfaUfaAfL96 | 16 | AS-12 | us(Ufo)saUfaGfaGfcAfagaAfcAfcUfgUfususu | 34 | 4.32 |
| AD-13 | S-13 | AfsasCfaGfuGfuUfCfUfuGfcUfcUfaUfaAfL96 | 17 | AS-13 | usUfsa(Ufo)aGfaGfcAfagaAfcAfc(Ufo)g(Ufo)ususu | 35 | 0.29 |
| AD-14 | S-14 | AfsasCfaGfuGfuUfCf(dTo)uGfcUfcUfaUfaAfL96 | 18 | AS-14 | usUfsaUfaGfaGfcAfagaAfcAfcUfgUfususu | 36 | 0.22 |
| AD-15 | S-15 | AfsasCfaGfuGfuUfCUfuGfcUfcUfaUfaAfL96 | 19 | AS-15 | us(dTos)aUfaGfaGfcAfagaAfcAfcUfgUfususu | 37 | na |

TABLE 1-continued

In vitro potency of 4'-modified siRNAs: Ufo = 4'-methoxy-2'-deoxy-2'-fluoro-uridine; dTo = 4'-methoxy-2'-deoxy-thymidine. Nf = 2'-deoxy-2'-fluoro-nucleotide. n = 2'-O-methyl-nucleotide. dT = 2'-deoxy-thymidine, s = phosphorothioate. L96 = GalNAc ligand.

| Duplex ID | Sense ID | Sense (5' to 3') | SEQ ID NO: | AS ID | Antisense (5' to 3') | SEQ ID NO: | IC50 (nM) |
|---|---|---|---|---|---|---|---|
| AD-16 | S-16 | AfsasCfaGfuGfuUfCfUfuGfcUfcUfaUfaAfL96 | 20 | AS-16 | usUfsa(dTo)aGfaGfcAfagaAfcAfc(dTo)gusu(dTo)us | 38 | 0.21 |
| AD-17 | S-17 | asascaguguucdTugcucUauaaL96 | 21 | AS-17 | usdTsauagagcdAagadAcacuguususu | 39 | na |
| AD-18 | S-18 | asascaguguucdTugcuc(dTo)auaaL96 | 22 | AS-18 | usdTsauagagcdAagadAcacuguususu | 40 | 0.25 |

Example 5. In Vivo Activity of the 4'-Modified siRNA Duplex (Prophetic)

4'-Modified siRNA duplex conjugated to a GalNAc ligand is administered to female C57BL/6 mice (6-10 weeks, 5 per group) via subcutaneous injection at a dose volume of 10 µl/g at a dose of 25, and 5 mg/kg siRNA. Control animals receive PBS by subcutaneous injection at the same dose volume.

After approximately 48 hours, mice are anesthetized with 200 µl of ketamine, and then exsanguinated by severing the right caudal artery. Liver tissue is collected, flash-frozen and stored at −80° C. until processing.

Efficacy of treatment can be evaluated by measurement of TTR mRNA in liver at 48 hours post-dose. TTR liver mRNA levels are assayed utilizing the Branched DNA assays-QuantiGene 1.0 (Panomics). Briefly, mouse liver samples are ground and tissue lysates are prepared. Liver lysis mixture (a mixture of 1 volume of lysis mixture, 2 volume of nuclease-free water and 10 µl of Proteinase-K/ml for a final concentration of 20 mg/ml) are incubated at 65° C. for 35 minutes. 5 ul of liver lysate and 95 µl of working probe set (TTR probe for gene target and GAPDH for endogenous control) are added into the Capture Plate. Capture Plates are incubated at 53° C.±1° C. (approximately 16-20 hours). The next day, the Capture Plates will be washed 3 times with 1× Wash Buffer (nuclease-free water, Buffer Component 1 and Wash Buffer Component 2), then dried by centrifuging for 1 minute at 240 g. 100 µl of Amplifier Probe mix per well is added into the Capture Plate, which is sealed with aluminum foil and incubated for 1 hour at 46° C.±1° C. Following 1 hour incubation, the wash step is repeated, then 100 µl of Label Probe mix per well is added. Capture plates are incubated at 46° C.±1° C. for 1 hour. The plates will then be washed with 1× Wash Buffer, dried and 100 µl Substrate per well is added into the Capture Plates. Capture Plates are incubated for 30 minutes at 46° C. followed by incubation for 30 minutes at room temperature. Plates are read using the SpectraMax Luminometer following incubation. bDNA data are analyzed by subtracting the average background from each duplicate sample, averaging the resultant duplicate GAPDH (control probe) and TTR (experimental probe) values, and then computing the ratio: (experimental probe-background)/(control probe-background). The average TTR mRNA level is calculated for each group and normalized to the PBS group average to give relative TTR mRNA as a percentage of the PBS control group.

4'-Modified siRNA non-conjugated duplex, formulated in a liposomal formulation is administered to female C57BL/6 mice (6-10 weeks, 5 per group) via intravenous injection at a dose volume of 10 µl/g at a dose of 25, and 5 mg/kg siRNA. Control animals receive PBS by intravenous injection at the same dose volume.

After approximately 48 hours, mice are anesthetized with 200 µl of ketamine, and then exsanguinated by severing the right caudal artery. Liver tissue is collected, flash-frozen and stored at −80° C. until processing.

Efficacy of treatment can be evaluated by measurement of TTR mRNA in liver at 48 hours post-dose. TTR liver mRNA levels are assayed utilizing the Branched DNA assays-QuantiGene 1.0 (Panomics). Briefly, mouse liver samples are ground and tissue lysates are prepared. Liver lysis mixture (a mixture of 1 volume of lysis mixture, 2 volume of nuclease-free water and 10 µl of Proteinase-K/ml for a final concentration of 20 mg/ml) are incubated at 65° C. for 35 minutes. 5 ul of liver lysate and 95 µl of working probe set (TTR probe for gene target and GAPDH for endogenous control) are added into the Capture Plate. Capture Plates are incubated at 53° C.±1° C. (approximately 16-20 hours). The next day, the Capture Plates will be washed 3 times with 1× Wash Buffer (nuclease-free water, Buffer Component 1 and Wash Buffer Component 2), then dried by centrifuging for 1 minute at 240 g. 100 µl of Amplifier Probe mix per well is added into the Capture Plate, which is sealed with aluminum foil and incubated for 1 hour at 46° C.±1° C. Following 1 hour incubation, the wash step is repeated, then 100 µl of Label Probe mix per well is added. Capture plates are incubated at 46° C.±1 OC for 1 hour. The plates will then be washed with 1× Wash Buffer, dried and 100 µl Substrate per well is added into the Capture Plates. Capture Plates are incubated for 30 minutes at 46° C. followed by incubation for 30 minutes at room temperature. Plates are read using the SpectraMax Luminometer following incubation. bDNA data are analyzed by subtracting the average background from each duplicate sample, averaging the resultant duplicate GAPDH (control probe) and TTR (experimental probe) values, and then computing the ratio: (experimental probe-background)/(control probe-background). The average TITR mRNA level is calculated for each group and normalized to the PBS group average to give relative TTR mRNA as a percentage of the PBS control group.

Figure 2A:
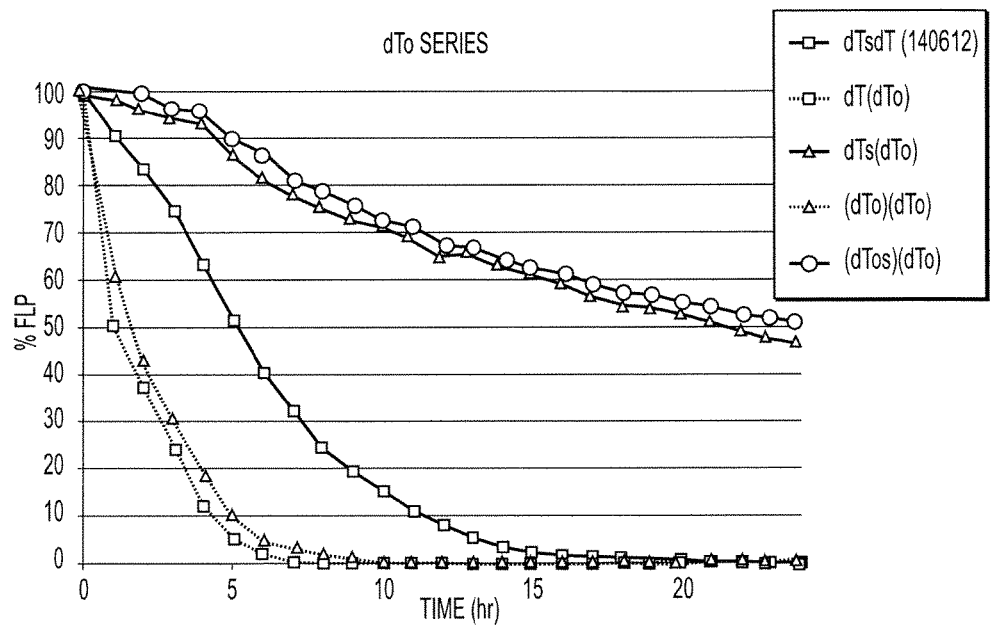
FIG. 2A shows the degradation of poly-deoxythymidine phosphodiester oligonucleotides containing 4'-modified nucleotides incubated with snake venom phosphodiesterase (SVPD). dTo series include compounds A-1 to A-4, as shown in Table 2.
Figure 2B:
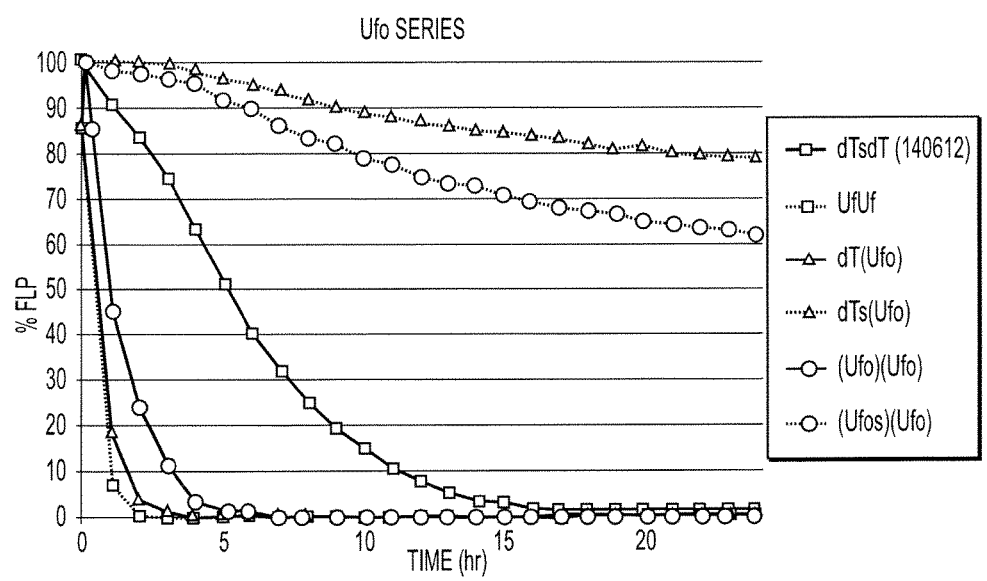
FIG. 2B shows the degradation of poly-deoxythymidine phosphodiester oligonucleotides containing 4'-modified nucleotides incubated with snake venom phosphodiesterase (SVPD). Ufo series include compounds A-5 to A-10, as shown in Table 2.

Example 6. Stability of 4'-Modification Against Exonucleases Snake Venon Phosphodiesterases (SVPD) Assay To access the stability of the 4'-modified oligonucleotides, 3'-exonuclease Snake Venon Phosphodiesterases (SVPD) assay was carried out according to the protocol described in Rajeev et al. (see Rajeev, K. G.; Prakash, T. P.; Manoharan, M., "2'-Modified-2-thiothymidine Oligonucleotides," Organic Lett. 5 (17): 3005-3008 (2003), and its supporting information, the content of which are herein incorporated by reference in their entirety). Solutions of the single strand oligonucleotides containing the 4'-modified nucleotides at the 3'-extremity were prepared at 0.1 mg/mL concentrations in 50 mM TRIS-HCl (pH 8) buffer, containing 10 mM MgCl$_2$. 1 mU/mL Snake venom phosphodiesterase I (Sigma-Aldrich) was added to the oligonculeotide mixture prior to first injection and kinetics were monitored for 24 hours at room temperature. Time points were injected directly on the analytical IEX-HPLC column from same sample preparation and analyzed by ion exchange HPLC using a Dionex DNAPac PA200 column at 30° C. A salt gradient of 37% to 52% of 1 M Sodium Bromide, 10% Acetonitrile, 20 mM Sodium Phosphate buffer at pH 11 was used to analyze each sample. UV integration of the 260 nm chromatograms was used to quantify the peaks and integration area ratios were plotted in order to obtain the decay curves of decomposition. All 4'-modified oligonculeotides demonstrated significantly enhanced resistance to SVPD exonuclease degradation of approximately 10- to 30-fold as described below. See Table 2 and FIG. 2.

TABLE 2

Half-Lifes of poly-deoxythymidine phosphodiester oligonucleotides containing 4'-modified nucleotides incubated with snake venom phosphodiesterase (SVPD).

| Seq ID | Sequence 5'-3' | Half Life [h] | Relative stability to dT18dTsdT control |
|---|---|---|---|
| Control | dTdTdTdTdTdTdTdTdTdTdTdTdTdTdTdTdTdTdTsdT | 2.18 | 1.00 |
| A-1 | dTdTdTdTdTdTdTdTdTdTdTdTdTdTdTdTdTdTdT(dTo) | 0.97 | 0.44 |
| A-2 | dTdTdTdTdTdTdTdTdTdTdTdTdTdTdTdTdTdTdTs(dTo) | 20.74 | 9.51 |
| A-3 | dTdTdTdTdTdTdTdTdTdTdTdTdTdTdTdTdTdTdT(dTo)(dTo) | 1.17 | 0.54 |
| A-4 | dTdTdTdTdTdTdTdTdTdTdTdTdTdTdTdTdTdTdT(dTos)(dTo) | 22.14 | 10.16 |
| A-5 | dTdTdTdTdTdTdTdTdTdTdTdTdTdTdTdTdTdTdTUfUf | 0.27 | 0.12 |
| A-6 | dTdTdTdTdTdTdTdTdTdTdTdTdTdTdTdTdTdTdTUfsUf | 7.38 | 3.39 |
| A-7 | dTdTdTdTdTdTdTdTdTdTdTdTdTdTdTdTdTdTdT(Ufo) | 0.42 | 0.19 |
| A-8 | dTdTdTdTdTdTdTdTdTdTdTdTdTdTdTdTdTdTdTs(Ufo) | 63.89 | 29.31 |
| A-9 | dTdTdTdTdTdTdTdTdTdTdTdTdTdTdTdTdTdTdT(Ufo)(Ufo) | 0.78 | 0.36 |
| A-10 | dTdTdTdTdTdTdTdTdTdTdTdTdTdTdTdTdTdTdT(Ufos)(Ufo) | 31.67 | 14.53 |

All 4'-modified oligonculeotides demonstrated significantly enhanced resistance to SVPD exonuclease degradation of approximately 10- to 30-fold.
Half-lifes were calculated from the Excel decay curves using Excel Fit.
Ufo = 4'-methoxy-2'-deoxy-2'-fluoro-uridine;
dTo = 4'-methoxy-2'-deoxy-thymidine;
Uf = 2'-deoxy-2'-fluoro-uridine;
dT = 2'-deoxy-thymidine,
s = phosphorothioate.
(dTo) 4'-methoxy-2'-deoxythymidine-3'-phosphate
(dTos) 4'-methoxy-2'-deoxythymidine-3'-phosphorothioate
(Ufo) 2'-fluoro-4'-methoxyuridine-3'-phosphate
(Ufos) 2'-fluoro-4'-methoxyuridine-3'-phosphorothioate
dT 2'-deoxythymidine-3'-phosphate
dTs 2'-deoxythymidine-3'-phosphorothioate

We claim:

1. A double-stranded RNAi agent capable of inhibiting the expression of a target gene, comprising a sense strand and an antisense strand, each strand having 12 to 30 nucleotides, wherein the duplex comprises at least one 4'-modified moiety, represented by one of the following formulas in group i) or group ii):

i)

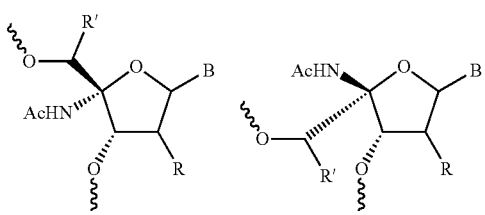

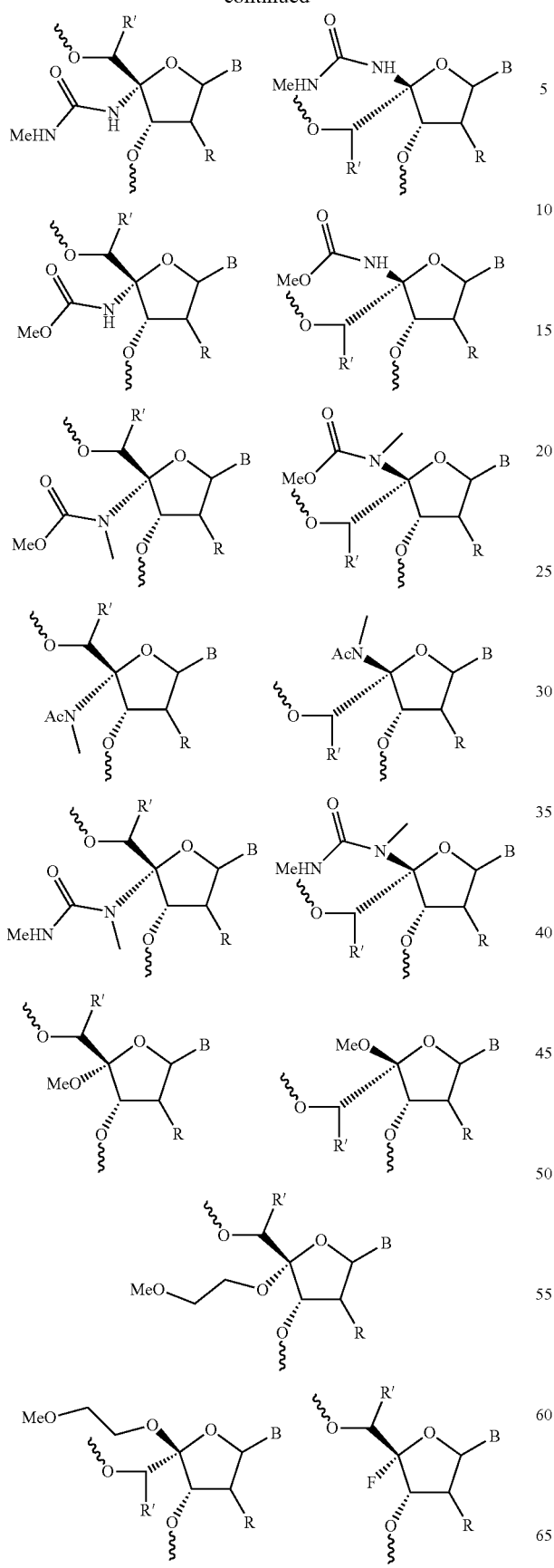
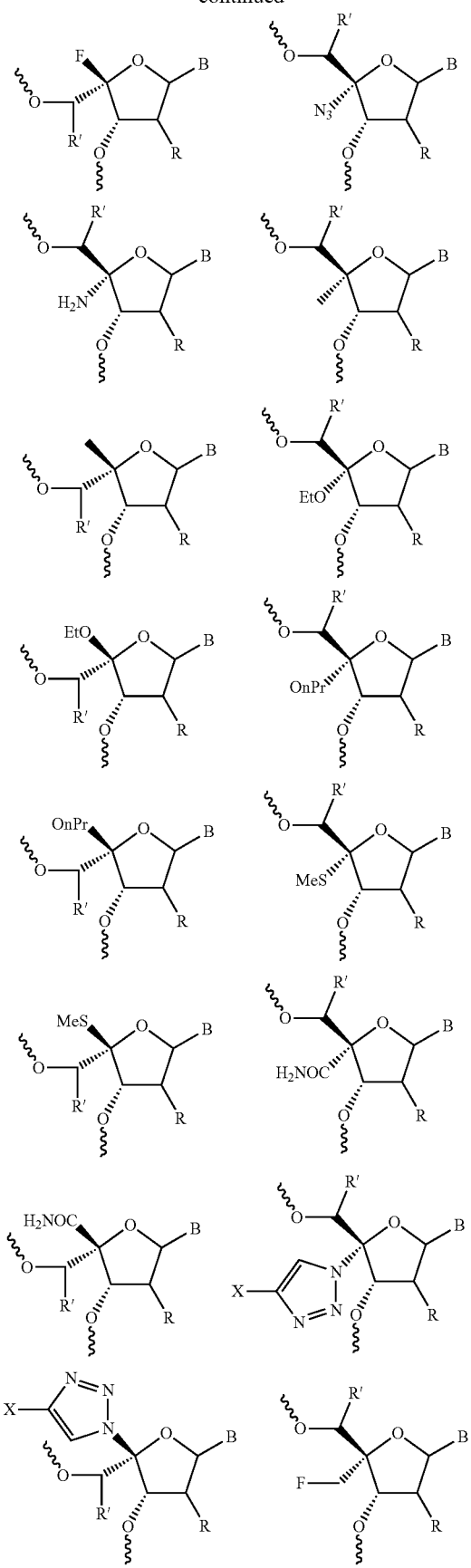

-continued

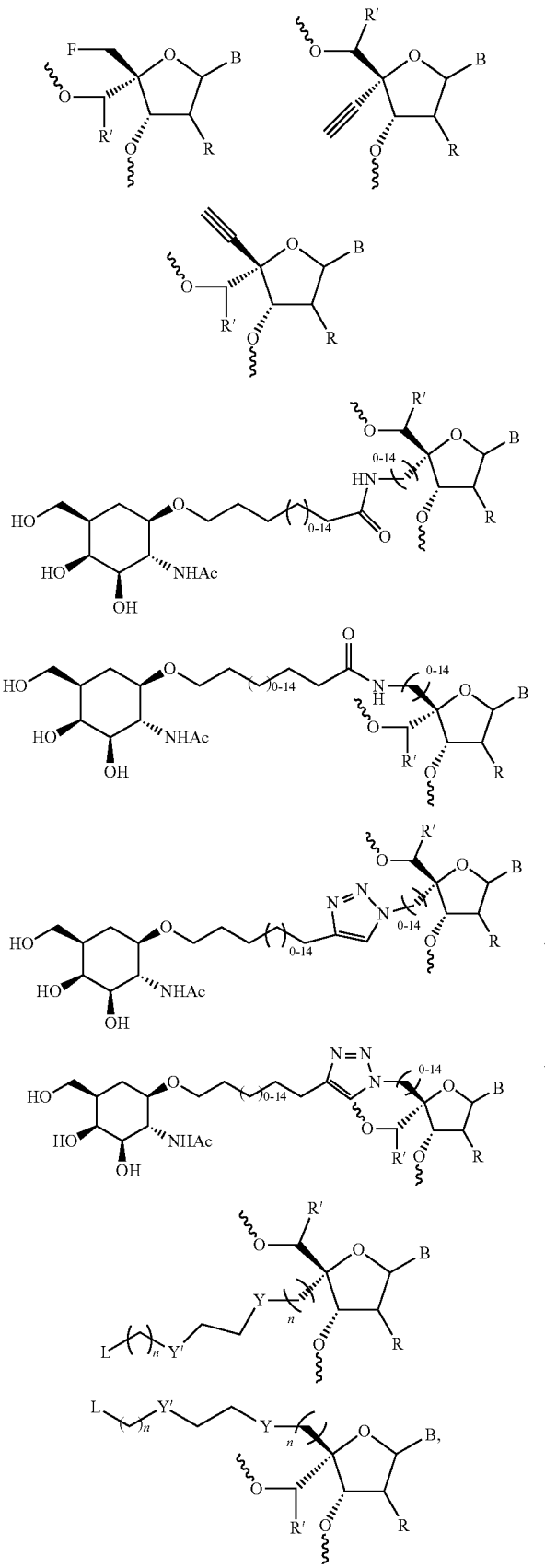

wherein:
R is independently H; OMe; F; OH; O-(CH$_2$)$_2$OMe; SMe, NMe$_2$; NH$_2$; Me; O-nPr; O-CH$_2$C(O)NHMe; O-(CH$_2$)$_2$NMe$_2$; O-(CH$_2$)$_2$O-(CH$_2$)$_2$ NMe$_2$; O-alkyl; or O-alkylamino;
R' is independently H or Me;
B is independently A; C; 5-Me-C; G; I; U; T; Y; 2-thiouridine; 4-thiouridine; C5-modified pyrimidines; C2-modified purines; N8-modified purines; phenoxazine; G-clamp; or non-canonical mono, bi and tricyclic heterocycles,
Y and Y' are each independently for each occurrence absent, CO, NH, O, S, OC(O), NHC(O), CH$_2$, CH$_2$NH or CH$_2$O, O, S, S(O), SO$_2$, N(R$^N$), C(R')=C(R"), C≡C or C(O), NHCH(R)C(O), —C(O)—CH(R)—NH—, CO, CH=N—O,

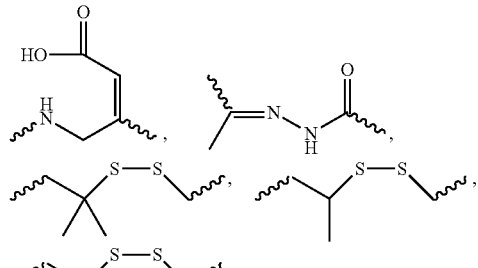

or heterocyclyl; and
n is independently an integer from 0 to 14;
L represents, in each occurrence, a ligand selected from the group consisting of a monosaccharide, disaccharide, trisaccharide, tetrasaccharide, oligosaccharide, polysaccharide, peptide, oligopeptide, RGD peptide, peptidoid, folate, cholesterol, lipid, and heterocycle; and
wherein the stereochemistry is R or S and combinations of R and S for the unspecified chiral centers;
or ii)

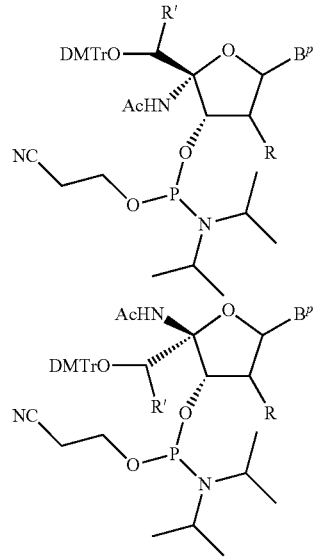

111
-continued
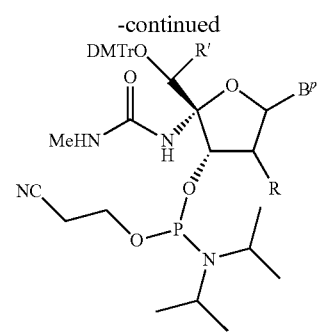
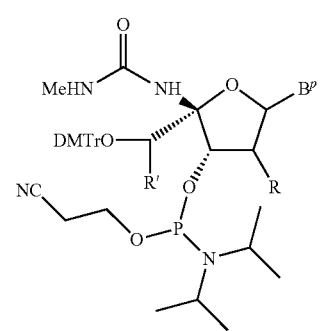
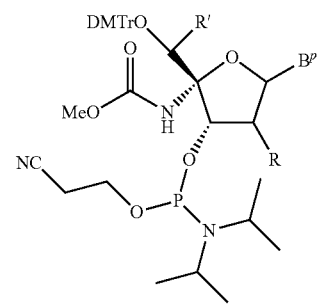
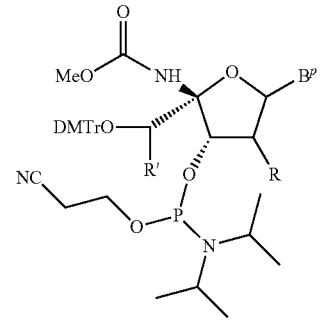
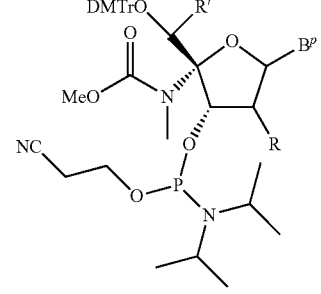
112
-continued
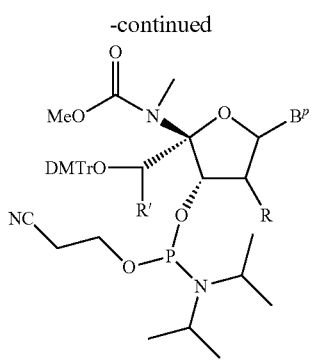
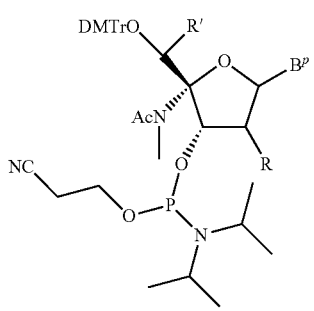
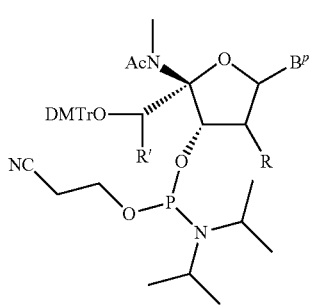
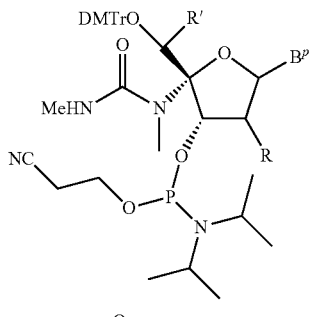
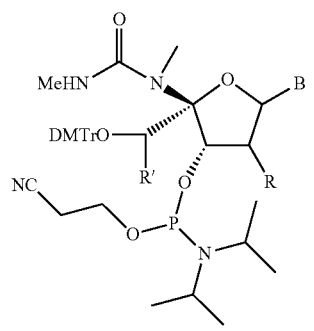

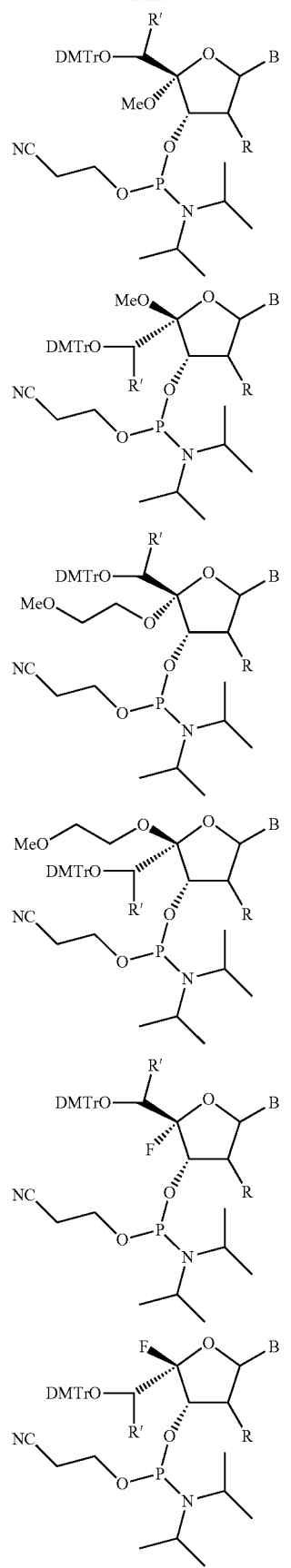
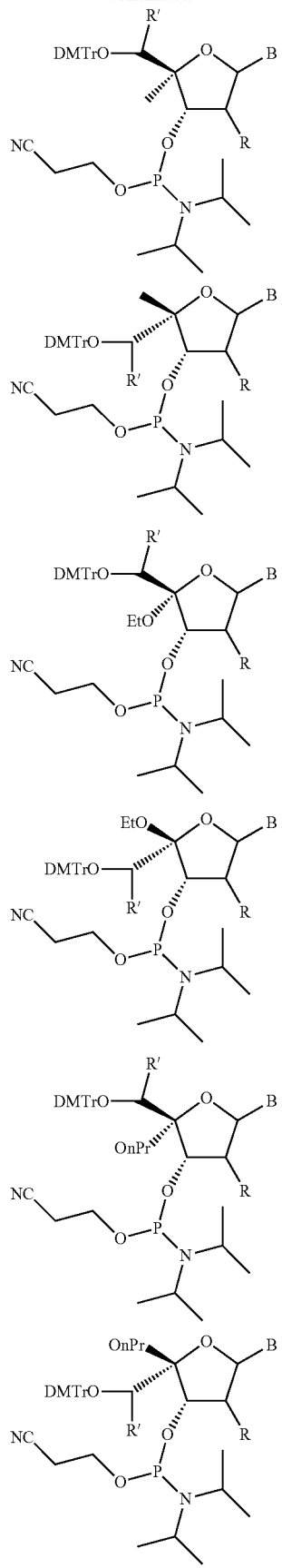

-continued

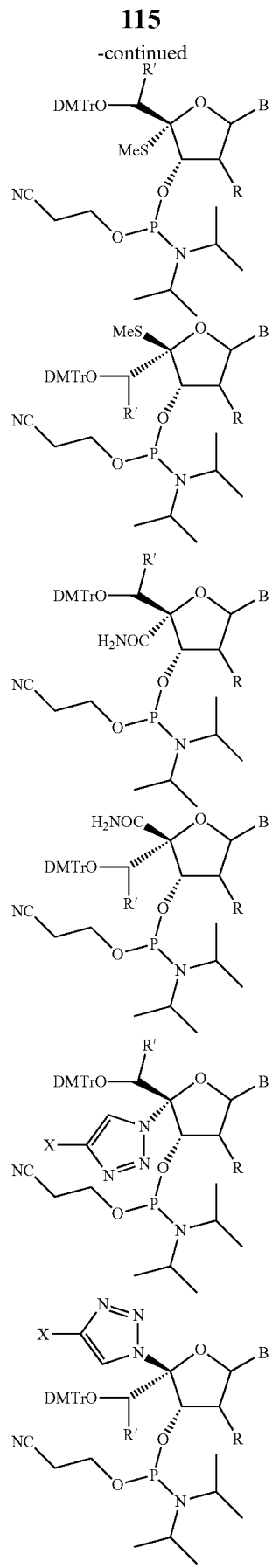

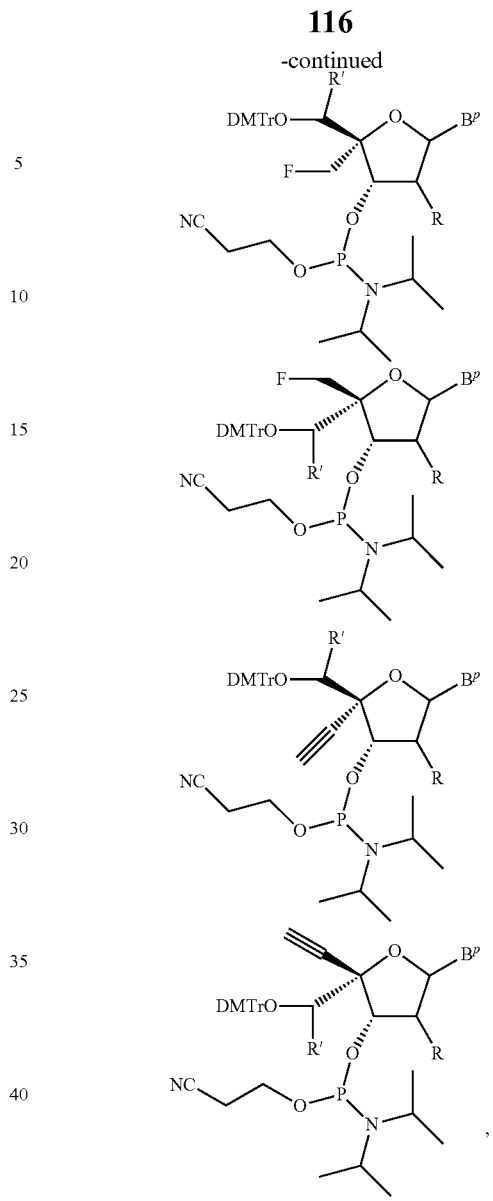

wherein:
R is independently H; OMe; OEt, F; OTBDMS; O-(CH$_2$)$_2$OMe; SMe, NMe$_2$; NPhth; Me; O-nPr; O-alkyl; or O-alkylamino;
R' is independently H or Me; and
B$^p$ and B are each independently A$^{Bz}$; C$^{Ac}$; 5-Me-C$^{Bz}$; G; I; U; T; Y; 2-thiouridine; 4-thiouridine; C5-modified pyrimidines; C2-modified purines; N8-modified purines; phenoxazine; G-clamp; or non-canonical mono, bi and tricyclic heterocycles,
wherein the stereochemistry is R or S and combinations of R and S for the unspecified chiral centers.

2. A double-stranded RNAi agent of claim 1, represented by formula (III):

sense: 5'$n_p$-N$_a$-(XXX)$_j$-N$_b$-YYY-N$_b$-(ZZZ)$_j$-N$_a$-$n_q$3' antisense: 3'$n_p$'-N$_a$'-(X'X'X')$_k$-N$_b$'-Y'Y'Y'-N$_b$'-(Z'Z'Z')$_l$-N$_a$'-$n_q$'5'    (III)

wherein:
j, k, and l are each independently 0 or 1;
p and q are each independently 0-6;

each Na and Na' independently represents an oligonucleotide sequence comprising 0-25 nucleotides which are either modified or unmodified or combinations thereof, each sequence comprising at least two differently modified nucleotides each Nb and Nb' independently represents an oligonucleotide sequence comprising 0-10 nucleotides which are either modified or unmodified or combinations thereof;

each $n_p$ and $n_q$ independently represents an overhang nucleotide; and

XXX, YYY, ZZZ, X'X'X', Y'Y'Y', and Z'Z'Z' each independently represent one motif of three identical modifications on three consecutive nucleotides;

wherein at least one of n, N, X, Y, or Z is a 4'-modified nucleoside of group i) or group ii); and wherein modifications on Nb is different than the modification on Y and modifications on Nb' is different than the modification on Y'.

3. The double-stranded RNAi agent of claim 1, wherein the duplex region is 17-30 nucleotide pairs in length.

4. The double-stranded RNAi agent of claim 1, wherein the duplex region is 17-19 nucleotide pairs in length.

5. The double-stranded RNAi agent of claim 1, wherein the duplex region is 27-30 nucleotide pairs in length.

6. The double-stranded RNAi agent of claim 1, wherein each strand has 17-30 nucleotides.

7. The double-stranded RNAi agent of claim 1, further comprising at least one ligand.

8. The double-stranded RNAi agent of claim 7, wherein the ligand is a one or more GalNAc derivatives attached through a bivalent or trivalent branched linker.

9. The double-stranded RNAi agent of claim 8, wherein the ligand is

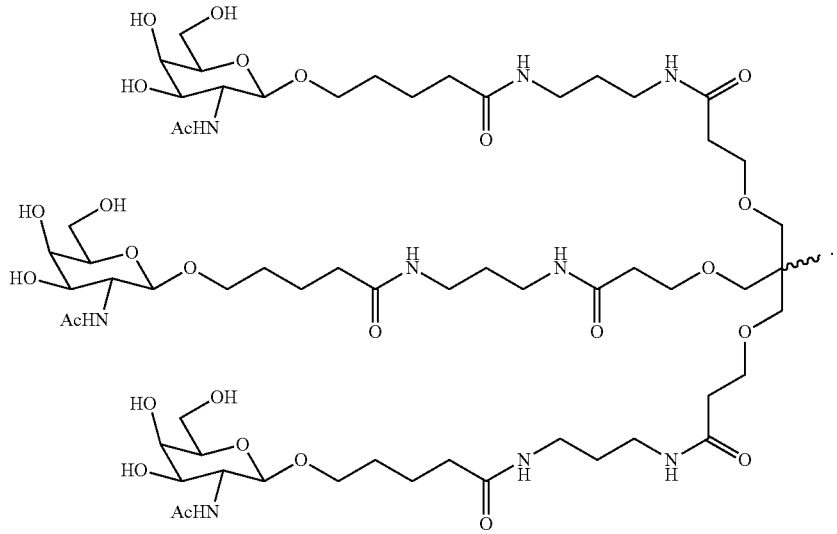 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

10. The double-stranded RNAi agent of claim 7, wherein the ligand is attached to the 3' end of the sense strand.

11. The double-stranded RNAi agent of claim 1, further comprising at least one phosphorothioate or methylphosphonate internucleotide linkage.

12. The double-stranded RNAi agent of claim 1, wherein the nucleotide at the 1 position of the 5'-end of the duplex in the antisense strand is selected from the group consisting of A, dA, dU, U, and dT.

13. The double-stranded RNAi agent of claim 1, wherein the base pair at the 1 position of the 5'-end of the duplex is an AU base pair.

14. The double-stranded RNAi agent of claim 2, wherein the Y nucleotides contain a 2'-fluoro modification.

15. The double-stranded RNAi agent of claim 2 wherein the Y' nucleotides contain a 2'-O-methyl modification.

16. A pharmaceutical composition comprising the double-stranded RNAi agent of claim 1, alone or in combination with a pharmaceutically acceptable carrier or excipient.

17. A method for inhibiting the expression of a target gene comprising the step of administering the double-stranded RNAi agent of claim 1, in an amount sufficient to inhibit expression of the target gene.

18. The method of claim 17, wherein the double-stranded RNAi agent is administered through subcutaneous or intravenous administration.

* * * * *

UNITED STATES PATENT AND TRADEMARK OFFICE
CERTIFICATE OF CORRECTION

PATENT NO. : 10,119,136 B2
APPLICATION NO. : 15/110658
DATED : November 6, 2018
INVENTOR(S) : Muthiah Manoharan et al.

Page 1 of 6

It is certified that error appears in the above-identified patent and that said Letters Patent is hereby corrected as shown below:

In the Claims

In Claim 1, Column 108, between Lines 34 and 42, delete " 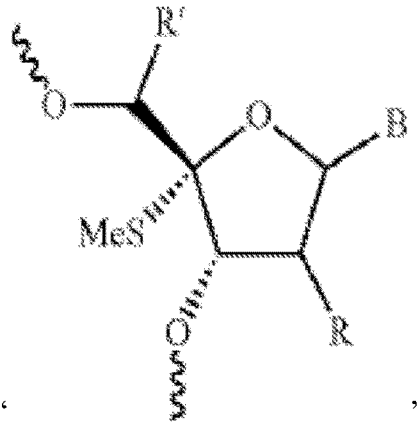 " and insert in its place -- 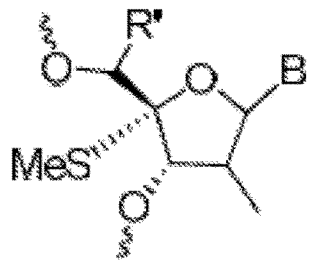 --.

Signed and Sealed this
Thirtieth Day of April, 2024

Katherine Kelly Vidal
*Director of the United States Patent and Trademark Office*

CERTIFICATE OF CORRECTION (continued)
U.S. Pat. No. 10,119,136 B2

Page 2 of 6

In Claim 1, Column 109, between Lines 22 to 28, delete

" 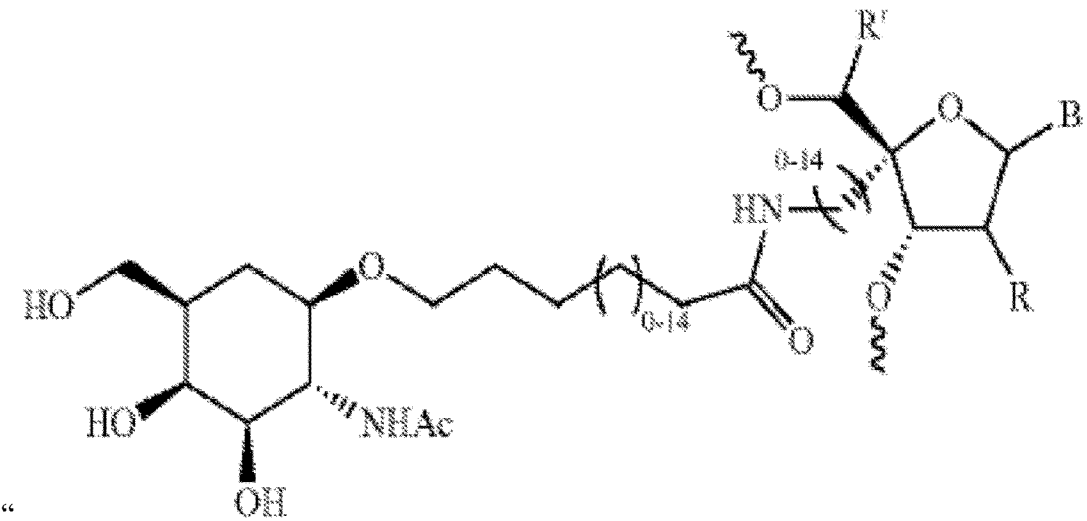 " and insert in its place

-- 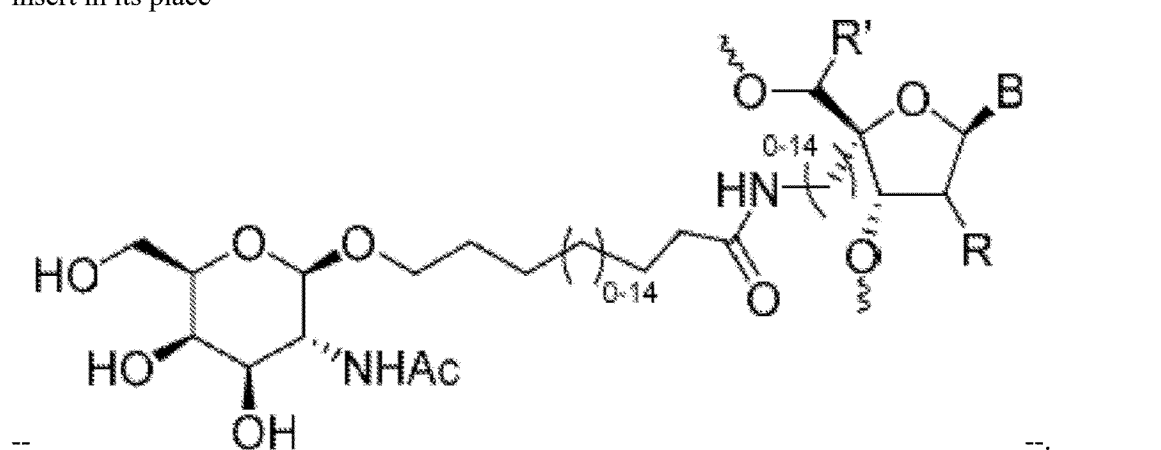 --.

In Claim 1, Column 109, between Lines 29 and 35, delete

" 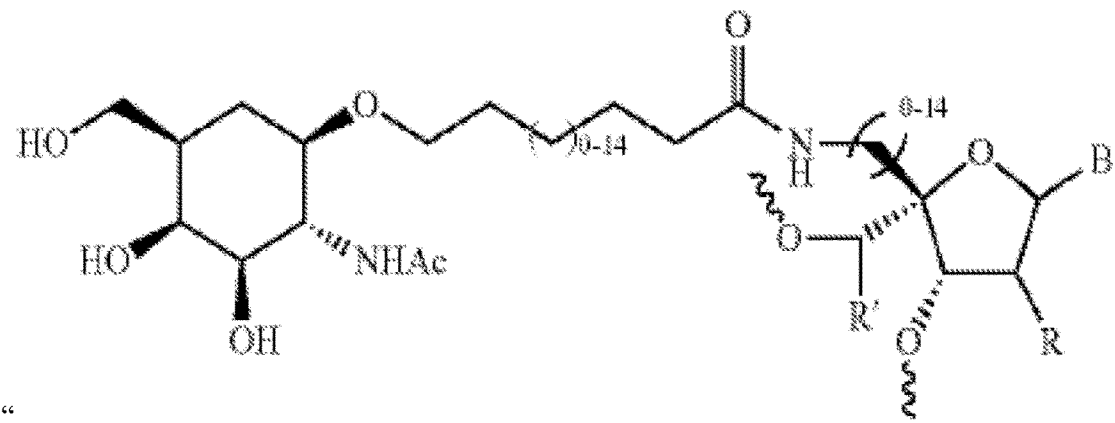 " and insert in its place

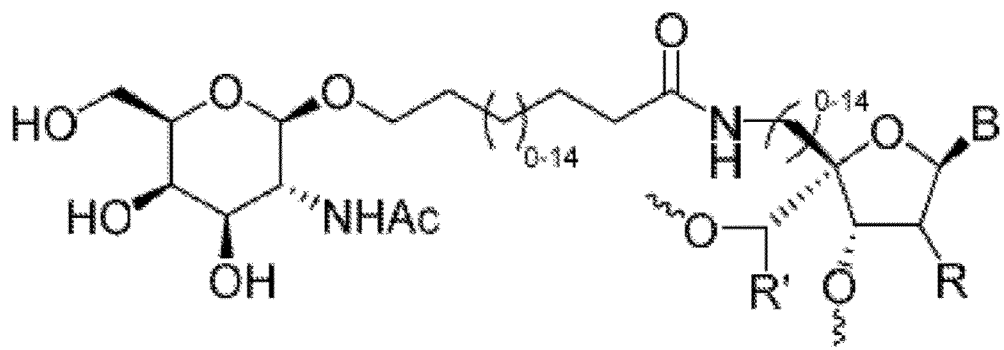
--  --.
In Claim 1, Column 109, between Lines 36 and 43, delete
"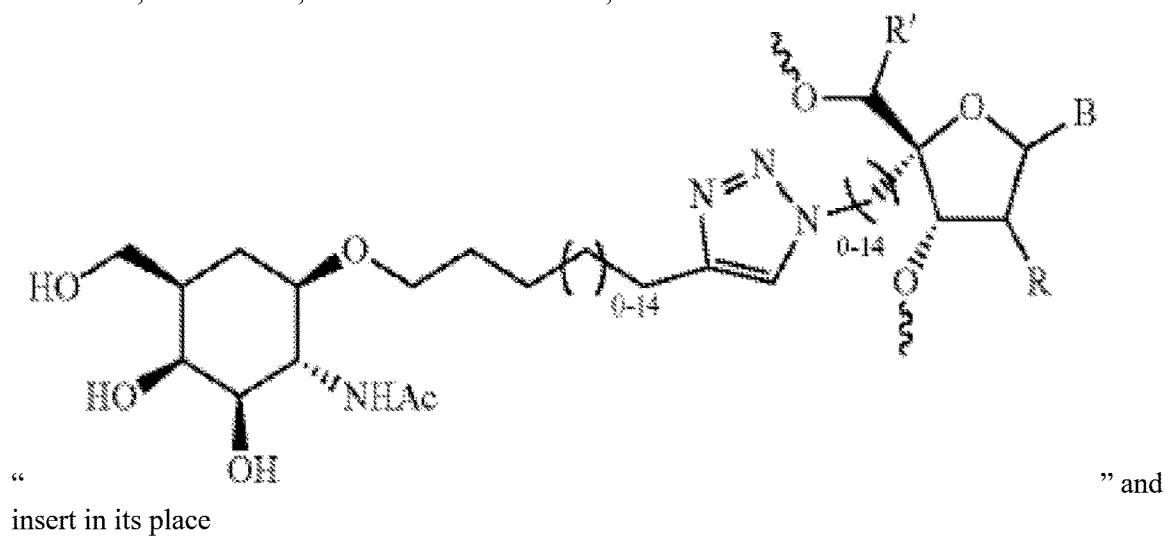" and
insert in its place
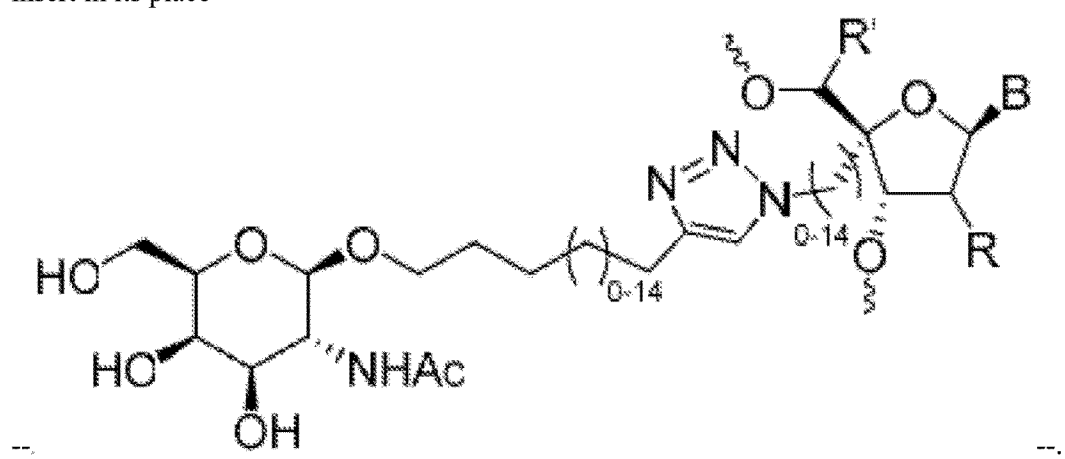
--,  --.
In Claim 1, Column 109, between Lines 44 and 50, delete

CERTIFICATE OF CORRECTION (continued)
U.S. Pat. No. 10,119,136 B2

" 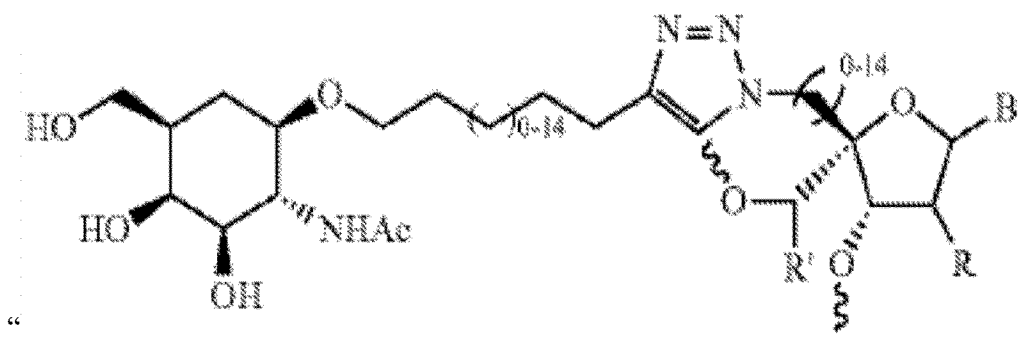 " and insert in its place

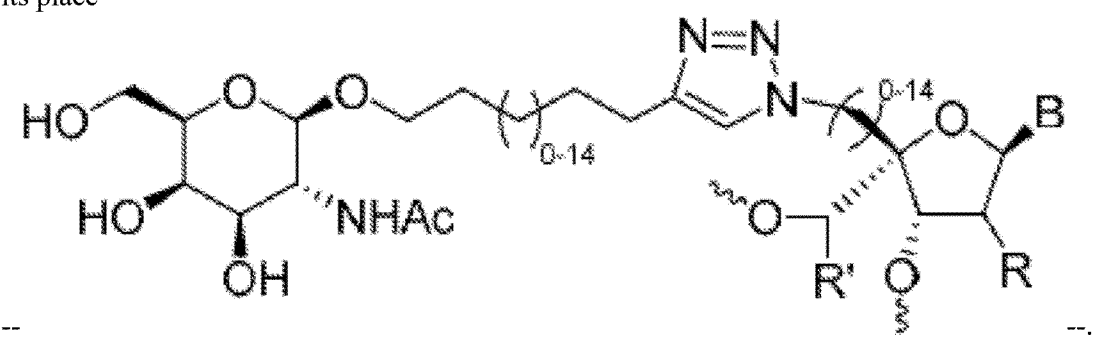 --.

In Claim 1, Column 109, between Lines 51 and 58, delete

" 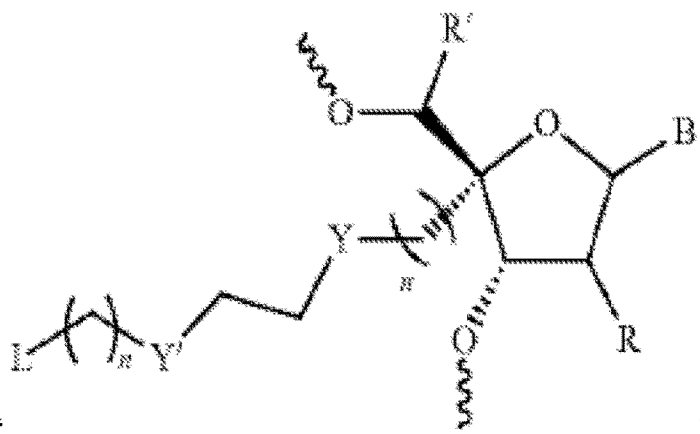 " and insert in its place

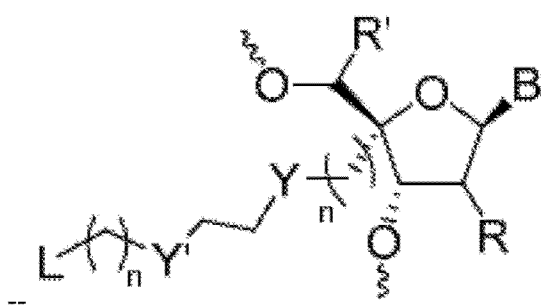 --.

In Claim 1, Column 109, between 59 and 65, delete

CERTIFICATE OF CORRECTION (continued)

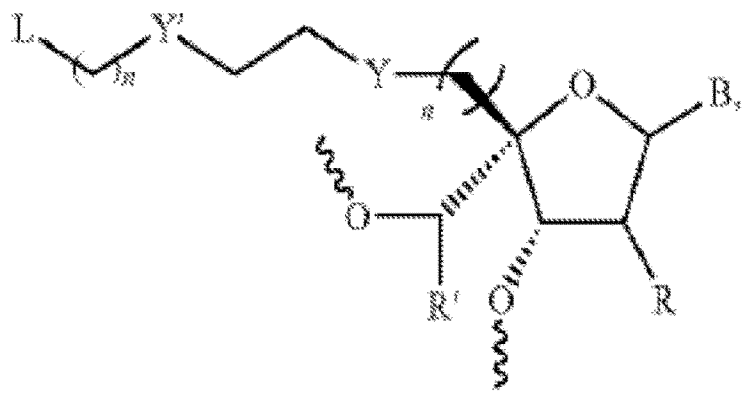

" and insert in its place

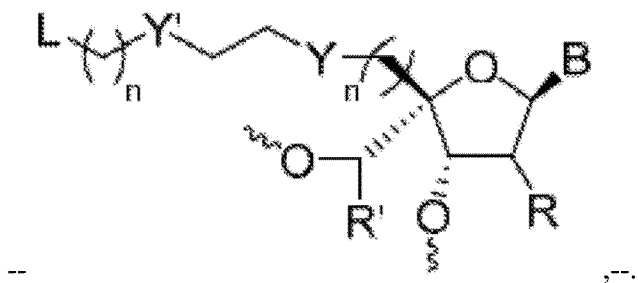

,--.

In Claim 1, Column 115, between Lines 1-8, delete " 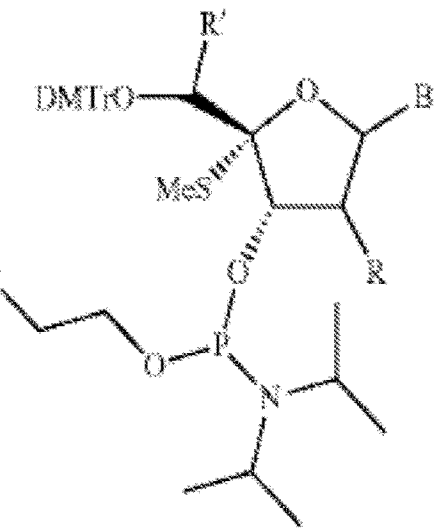 " and insert in its place -- 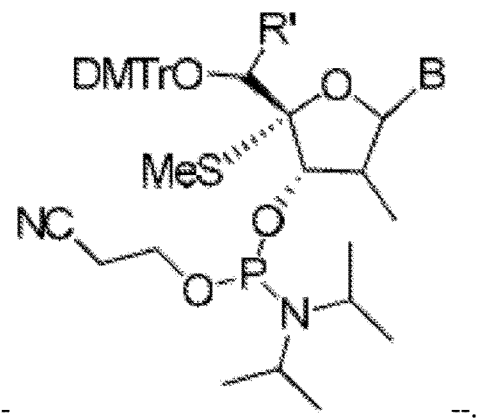 --.
In Claim 2, Column 116, in Line 66, delete "j, k, and l are each independently 0 or 1;" and insert in its place --i, j, k, and l are each independently 0 or 1;--.

SEQUENCE LISTING

<160> NUMBER OF SEQ ID NOS: 51

<210> SEQ ID NO 1
<211> LENGTH: 16
<212> TYPE: PRT
<213> ORGANISM: Unknown
<220> FEATURE:
<223> OTHER INFORMATION: Description of Unknown: RFGF
      peptide

<400> SEQUENCE: 1

Ala Ala Val Ala Leu Leu Pro Ala Val Leu Leu Ala Leu Leu Ala Pro
1               5                   10                  15

<210> SEQ ID NO 2
<211> LENGTH: 11
<212> TYPE: PRT

```
<213> ORGANISM: Unknown
<220> FEATURE:
<223> OTHER INFORMATION: Description of Unknown: RFGF
      analogue peptide

<400> SEQUENCE: 2

Ala Ala Leu Leu Pro Val Leu Leu Ala Ala Pro
1               5                   10

<210> SEQ ID NO 3
<211> LENGTH: 13
<212> TYPE: PRT
<213> ORGANISM: Human immunodeficiency virus

<400> SEQUENCE: 3

Gly Arg Lys Lys Arg Arg Gln Arg Arg Pro Pro Gln
1               5                   10

<210> SEQ ID NO 4
<211> LENGTH: 16
<212> TYPE: PRT
<213> ORGANISM: Drosophila sp.

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ugacaaaaua acucacuaua a                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugacaaaaua acucacuaua a                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ugacaaaaua acucacuaua a                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 8
ugacaaaaua acucacuaua a                                                    21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugacaaaaua acucacuaua a                                                    21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ugacaaaaua acucacuaua a                                                    21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ugacaaaaua acucacuaua a                                                    21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ugacaaaaua acucacuaua a                                                    21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ugacaaaaua acucacuaua a                                                    21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 14
aacaguguuc uugcucuaua a                                         21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aacaguguuc uugcucuaua a                                         21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
aacaguguuc uugcucuaua a                                         21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aacaguguuc uugcucuaua a                                         21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
aacaguguuc tugcucuaua a                                         21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
aacaguguuc uugcucuaua a                                         21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
                         oligonucleotide

<400> SEQUENCE: 20
aacaguguuc uugcucuaua a                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
aacaguguuc tugcucuaua a                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
aacaguguuc tugcuctaua a                                              21

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uuauagugag uuauuuuguc aau                                            23

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uuauagugag uuauuuuguc aau                                            23

<210> SEQ ID NO 25
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuauagugag uuauuuuguc aau                                            23

<210> SEQ ID NO 26
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uuauagugag uuauuuuguc aau                                              23

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uuauagugag uuauuuuguc aau                                              23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
uuauagugag uuatuuuguc aau                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
utauagugag uuauutuguc aau                                              23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
uuatagugag uuauutuguc aau                                              23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
          oligonucleotide
<220> FEATURE:
<223> OTHER INFORMATION: Description of Combined DNA/RNA Molecule:
      Synthetic oligonucleotide

<400> SEQUENCE: 31
uuatagugag uuauutuguc aau                                          23

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uuauagagca agaacacugu uuu                                          23

<210> SEQ ID NO 33
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uuauagagca agaacacugu uuu                                          23

<210> SEQ ID NO 34
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uuauagagca agaacacugu uuu                                          23

<210> SEQ ID NO 35
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uuauagagca agaacacugu uuu                                          23

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uuauagagca agaacacugu uuu                                          23

<210> SEQ ID NO 37
<211> LENGTH: 23
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
utauagagca agaacacugu uuu                                              23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
uuatagagca agaacactgt uuu                                              23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
utauagagca agaacacugu uuu                                              23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
utauagagca agaacacugu uuu                                              23

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tttttttttt tttttttttt                                                  20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 42
tttttttttt tttttttttt                                         20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tttttttttt tttttttttt                                         20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tttttttttt tttttttttt                                         20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tttttttttt tttttttttt                                         20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
tttttttttt tttttttuu                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
tttttttttt tttttttuu                                          20

<210> SEQ ID NO 48

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
tttttttttt tttttttttu                                                20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
tttttttttt tttttttttu                                                20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
tttttttttt ttttttttuu                                                20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
tttttttttt ttttttttuu                                                20
```